(12) United States Patent
Lombardo et al.

(10) Patent No.: US 11,564,675 B2
(45) Date of Patent: Jan. 31, 2023

(54) KNOTLESS INSTABILITY SUTURE ANCHOR CONSTRUCT AND SYSTEM

(71) Applicant: Conmed Corporation, Utica, NY (US)

(72) Inventors: Giuseppe Lombardo, New Port Richey, FL (US); Grady Breslich, Bradenton, FL (US)

(73) Assignee: Conmed Corporation, Utica, NY (US)

( * ) Notice: Subject to any disclaimer, the term of this patent is extended or adjusted under 35 U.S.C. 154(b) by 189 days.

(21) Appl. No.: 16/002,189

(22) Filed: Jun. 7, 2018

(65) Prior Publication Data

US 2018/0353167 A1 Dec. 13, 2018

Related U.S. Application Data

(60) Provisional application No. 62/518,344, filed on Jun. 12, 2017.

(51) Int. Cl.
*A61B 17/04* (2006.01)
*A61B 17/06* (2006.01)
(Continued)

(52) U.S. Cl.
CPC .... *A61B 17/0401* (2013.01); *A61B 17/06166* (2013.01); *A61B 17/17* (2013.01); *A61B 17/1615* (2013.01); *A61B 2017/0042* (2013.01); *A61B 2017/0053* (2013.01); *A61B 2017/0403* (2013.01); *A61B 2017/044* (2013.01); *A61B 2017/0406* (2013.01); *A61B 2017/0409* (2013.01); *A61B 2017/0448* (2013.01); *A61B 2017/0458* (2013.01); *A61B 2017/0459* (2013.01); *A61B 2017/0464* (2013.01);
(Continued)

(58) Field of Classification Search
CPC ........ A61B 2017/0404; A61B 17/0401; A61B 2017/0403–0409; A61B 2017/042; A61B 2017/0464; A61B 17/06166; A61B 17/17; A61F 2/0811
See application file for complete search history.

(56) References Cited

U.S. PATENT DOCUMENTS

2013/0190819 A1* 7/2013 Norton ............... A61B 17/0482
606/232
2013/0296934 A1* 11/2013 Sengun ................. A61B 17/04
606/232

(Continued)

*Primary Examiner* — Kelly J Bekker
*Assistant Examiner* — Andrew P. Restaino
(74) *Attorney, Agent, or Firm* — Bond, Schoeneck & King, PLLC; Frederick J. M. Price

(57) ABSTRACT

An anchor construct having an anchor having a length of suture material passing therethrough, the suture material having a loop strand terminating at a first end and a post strand terminating at a second end, a splice loop formed by first end, a sliding construct formed by the first end and the second end, wherein the sliding construct is configured to adjust the relative position of the splice loop and the anchor. The anchor construct can be deployed by passing the first end through a first body and through the splice, creating a locking loop of a first size around the first body, implanting the anchor into a bone hole, pulling the post strand to decrease the perimeter of the positioning loop to a second size smaller than the first size, and pulling the loop strand to decrease the perimeter of the locking loop to a smaller second size.

19 Claims, 30 Drawing Sheets

(51) Int. Cl.
  *A61B 17/17* (2006.01)
  *A61B 17/00* (2006.01)
  *A61B 17/16* (2006.01)
(52) U.S. Cl.
  CPC ................ *A61B 2017/0477* (2013.01); *A61B 2017/06185* (2013.01)

(56) References Cited

U.S. PATENT DOCUMENTS

2014/0277133 A1* 9/2014 Foerster ............. A61B 17/0401
   606/232
2015/0351739 A1* 12/2015 Napolitano ........ A61B 17/0401
   606/228

* cited by examiner

KNOTLESS INSTABILITY SUTURE ANCHOR CONSTRUCT AND SYSTEM

CROSS-REFERENCE TO RELATED APPLICATION

The present application relates and claims priority to U.S. Provisional Application No. 62/518,344 filed Jun. 12, 2017, the entirety of which is hereby incorporated by reference

BACKGROUND OF THE INVENTION

Field of the Invention

The present invention is related to a suture anchor device for soft tissue to bone repair in surgical procedures and, more particularly, to a knotless suture anchor with a sliding construct for tissue tensioning and a splice to secure the tissue in relative position to the bone.

Description of the Related Art

Suture anchors are commonly used to repair soft tissue to bone in surgical procedures, such as shoulder instability repair. Typically, the suture anchors are inserted into a pre-formed bone hole and then the sutures are passed through the tissue to be repaired. In many cases, a sliding knot is tied, which provides better tissue tensioning control and allows the surgeon to manipulate the sliding knot in order to bring the tissue into apposition to the bone. In doing so, the tissue is naturally brought back to the point of origin of the suture and comes to rest directly over the bone hole. To secure the sliding knot, the surgeon ties one or more alternating half-hitch knots to complete the procedure. The act of tying a knot presents a number of challenges to the surgeon, especially when doing so arthroscopically. Furthermore, in some cases, knots have been implicated as the source of post-operative pain caused by irritation from the knot stack.

Various types of suture anchors have been developed which fasten the suture in place without requiring the surgeon to tie a knot, as should be understood by those of skill in the art. Some designs capture the suture between two anchor components, while others utilize an interference fit between the anchor and the bone tunnel. Many designs using these methods of fixation require a driver to be engaged with the anchor while tensioning the suture in order to bring the tissue into apposition to the bone. Since the driver is still engaged in the bone hole when in use, it can prohibit tensioning of the tissue so that it is directly over the bone hole (suture origin) thus giving a less than ideal tissue position and encumbering the adjustment of suture tension.

Attempts at addressing the problem of tissue position include implementation of an adjustable loop which is formed around the tissue to be repaired. In this instance, the anchor is installed in the bone hole and then the driver is removed. One limb of the suture is free and is passed first through the tissue and then into a loading filament which passes it back through the suture limb to create a one-way loop. However, this requires the standing end of the suture to remain fixed so that it acts as a 'finger trap' when the loop is tensioned thereby preventing loop loosening. This method also requires a long length of suture to pass through or around the tissue before the loop is reduced which can cause damage by abrasion. Furthermore, the fixed end must reside deep in the hole and must not migrate or tensioning; will be limited. Lastly, this type of conventional device is comprised of a rigid material which can damage tissue if it is pulled out of the bone hole during healing.

Therefore, the inventors recognized that a need exists for a simple-to-use suture anchor comprised of soft materials which secures suture without the need to tie a knot, and which facilitates the ability to adjust, maintain, and position tissue in a desired location over the bone hole during anchor installation.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

Embodiments of the present invention recognize that there are potential problems and/or disadvantages with the conventional knot or knotless suture constructs. For example, knots and knotless constructs can be large and rigid enough to cause irritation, and require constant engagement by the driver during installation which results in less than ideal positioning of the tissue over the bone hole (as described above). Therefore, a need exists for a simple-to-use soft locking suture construct with a means for adjusting, maintaining and positioning tissue in a desired location over the bone hole during anchor installation. Various embodiments of the present invention may be advantageous in that they may solve or reduce one or more of the potential problems and/or disadvantages discussed herein.

The present disclosure is directed to an inventive configuration, structure, and resulting function of a knotless instability suture anchor construct and system. The knotless instability suture anchor construct includes an anchor with passing suture material having a first end and a second end, a splice loop at the first end, and a sliding construct (e.g. a knot) created by the first end and the second end. The sliding construct is configured to adjust the relative position of the splice loop and the anchor.

According to another aspect, a knotless instability suture anchor system is provided that includes a threader assembly having a cover and a back piece with a removable threader arm. The removable threader arm has a circular raised hook configured to maintain threader material in a threader loop. The cover has a pair of movable clips configured to lock into clip receiving apertures on a back piece. A channel extends through the threader assembly along both the back piece and the cover. The system also includes a knotless instability suture anchor construct having an anchor with passing suture material. The passing suture material has a first end and a second end, a splice at the first end, and a sliding construct created by the first end and the second end. The sliding construct adjusts the relative position of the splice and the anchor. The knotless instability anchor construct extends along the channel in the threader assembly, and a threader loop is secured around the hook of the threader arm.

The ends of the threader loop extend through the splice and outside the threader assembly.

According to an another aspect, a method of securing a first body in relative position to a bone hole includes (but is not limited to) the steps of: (i) providing a knotless instability suture anchor construct having an anchor with passing suture material including a first end and a second end, a splice positioned in the first end, a sliding construct created by the first end and the second end, wherein the sliding construct creates a positioning loop in the suture material of a first size with a perimeter defined at least in part by the anchor; (ii) passing the first end through a first body and through the splice; (iii) creating a locking loop of a first size around the first body; (iv) implanting the anchor into a bone hole; (v) pulling the post strand to decrease the perimeter of the positioning loop to a second size smaller than the first size; and (vi) pulling the loop strand to decrease the perimeter of the locking loop to a second size smaller than the first size.

Suture material or sutures, as the terms are used and described herein, include monofilament or multi-filament suture as well as any other metallic or non-metallic filamentary or wire-like material suitable for performing the function of a suture. This material can include both bioabsorbable and non-absorbable materials.

BRIEF DESCRIPTION OF THE SEVERAL VIEWS OF THE DRAWING(S)

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments.

Reference is now made briefly to the accompanying drawings, in which.

Figure 4A:
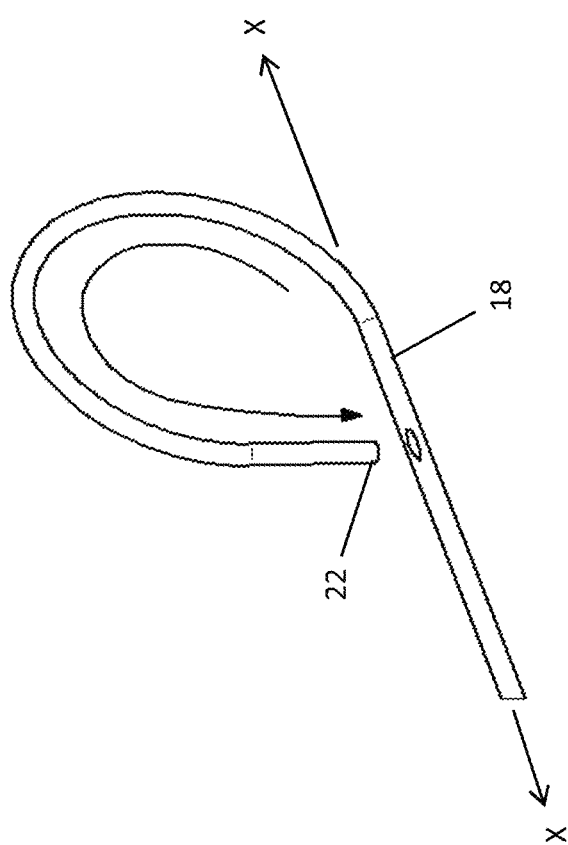
Figure 4B:
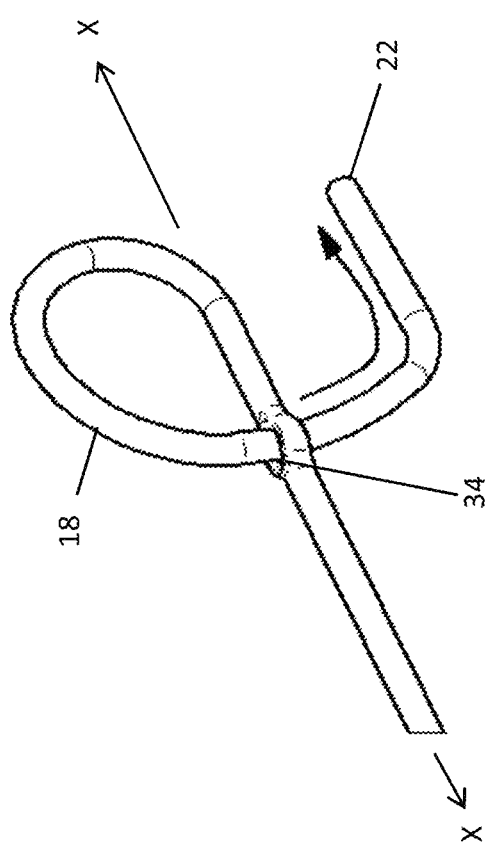
Figure 4C:
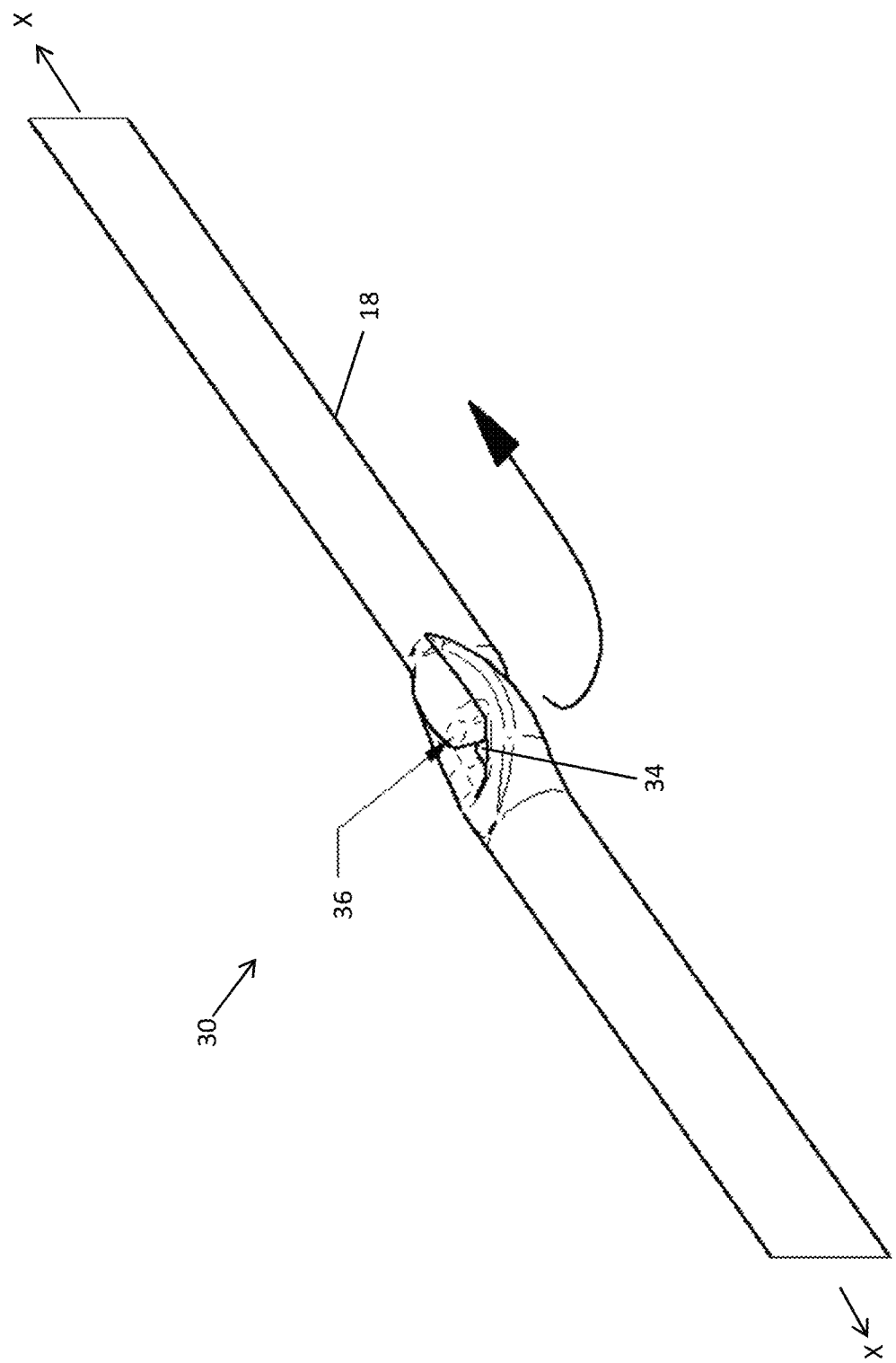
Figure 4D:
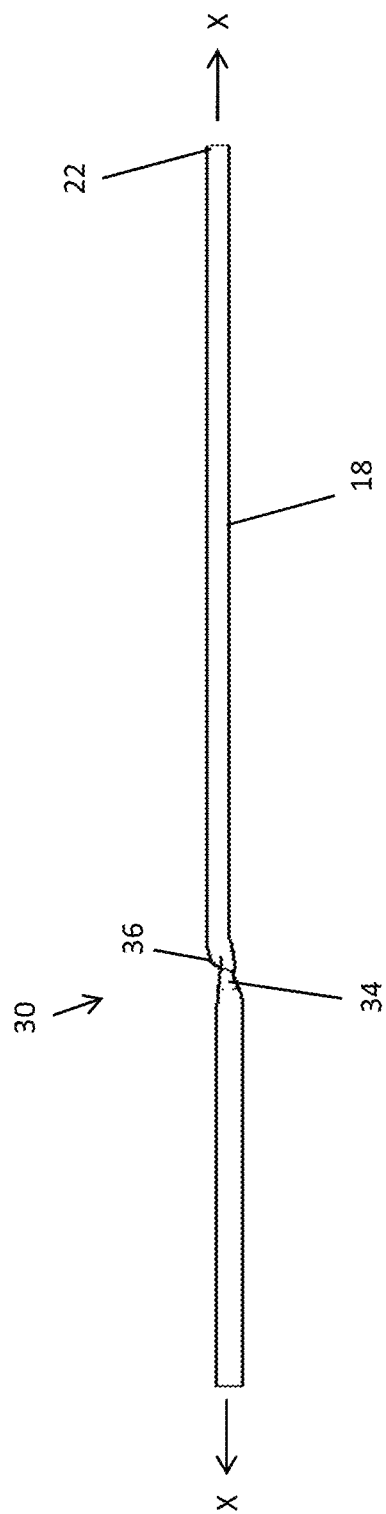
Figure 4E:
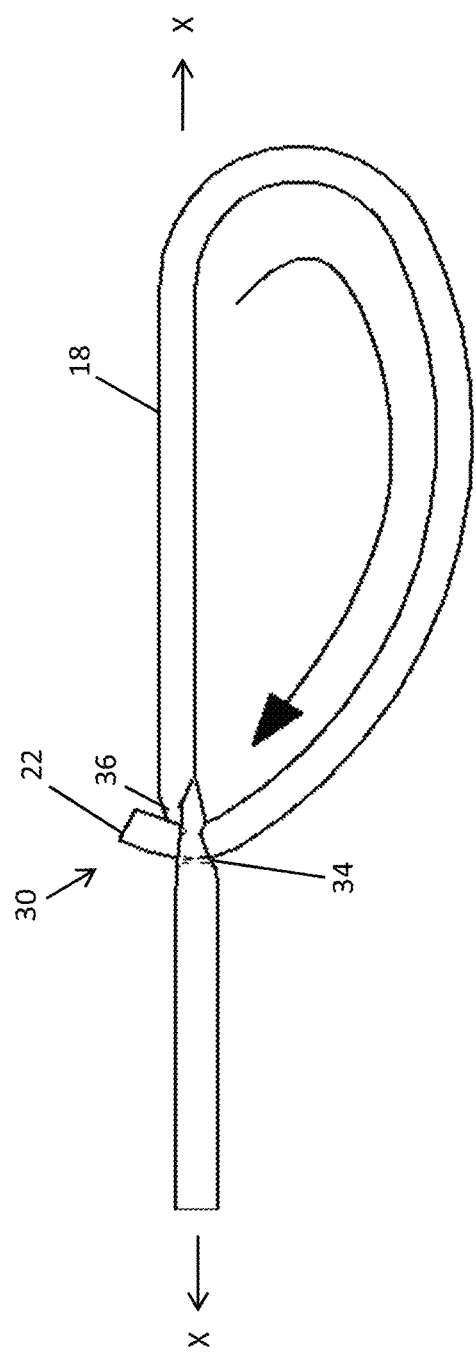
Figure 4F:
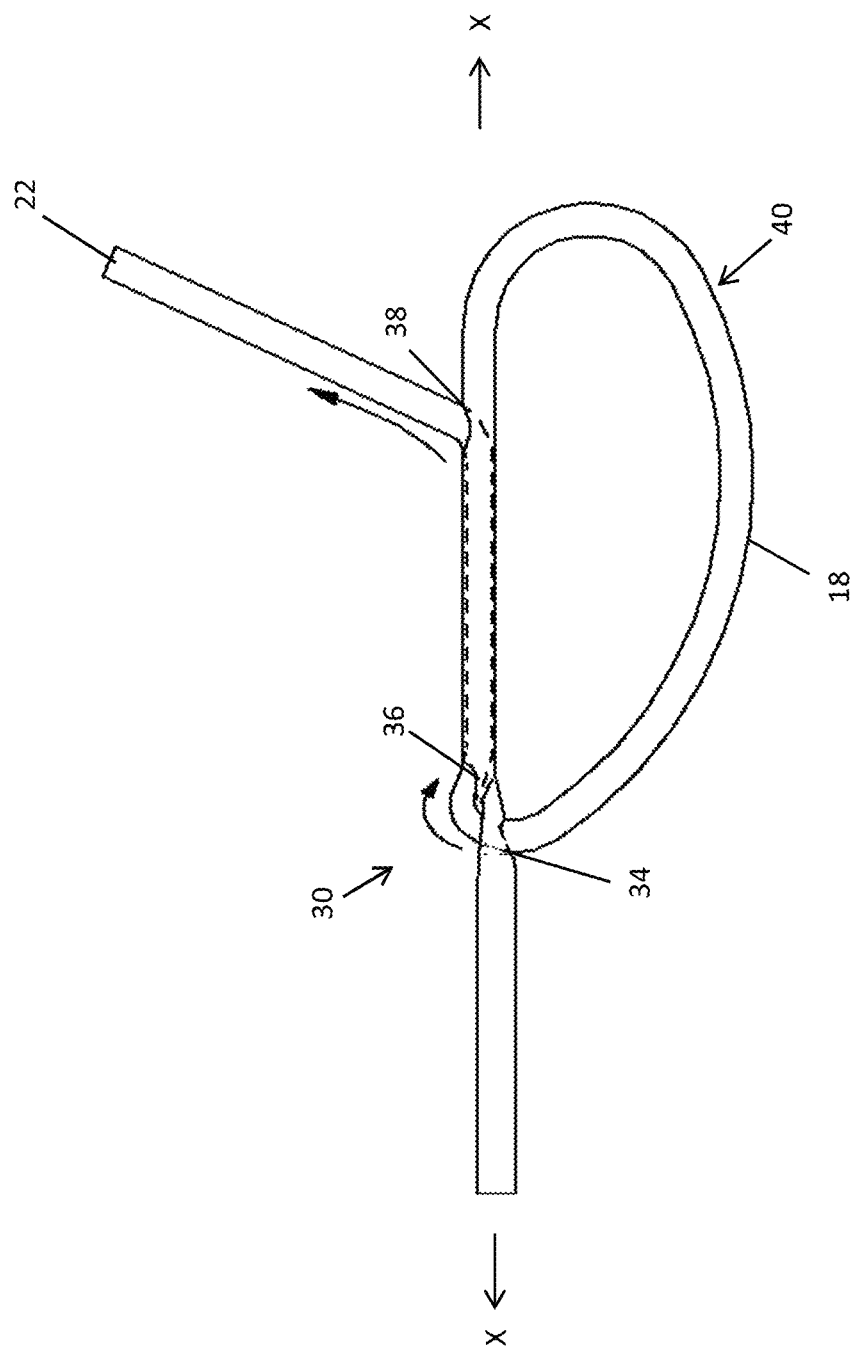
Figure 5:
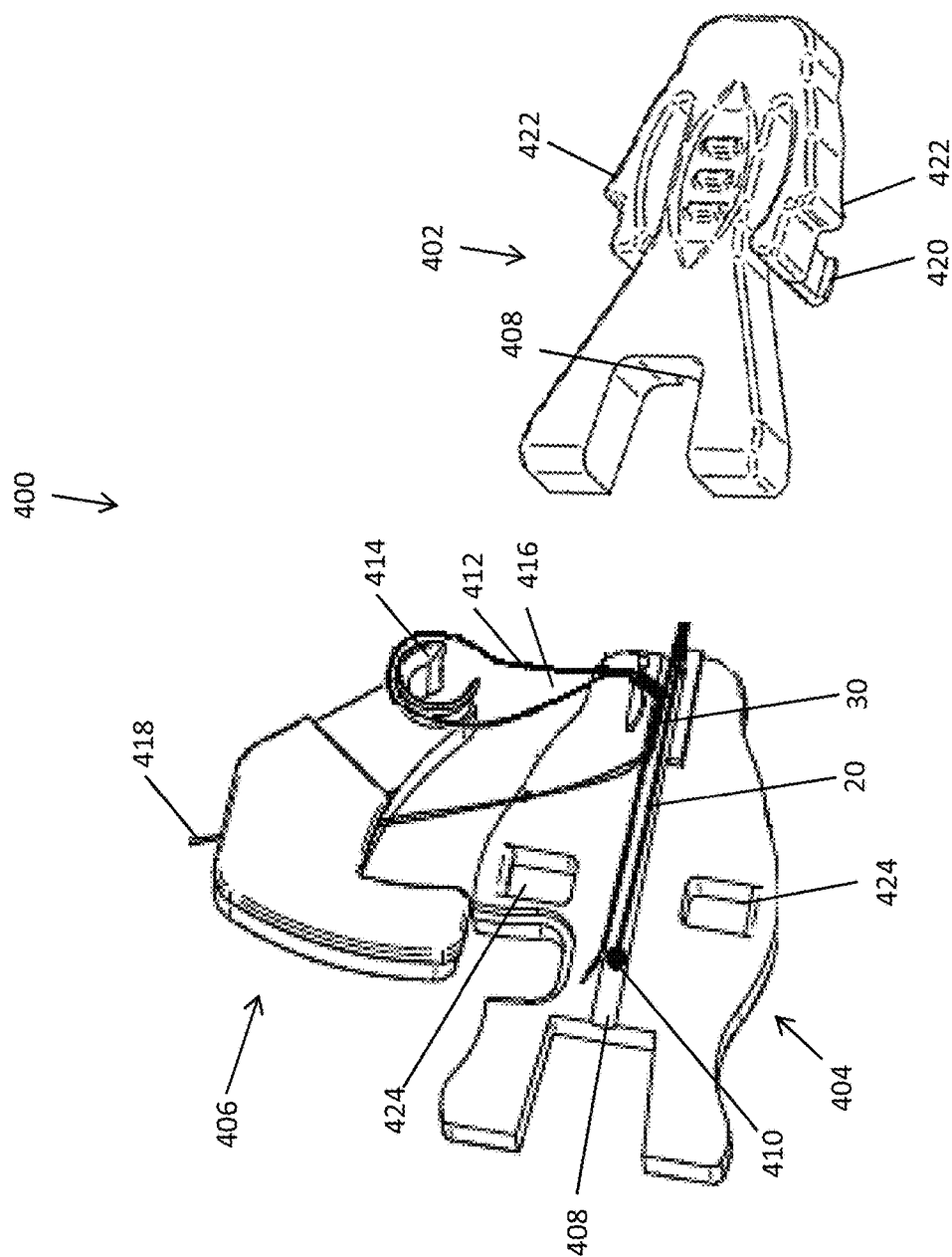
Figure 6:
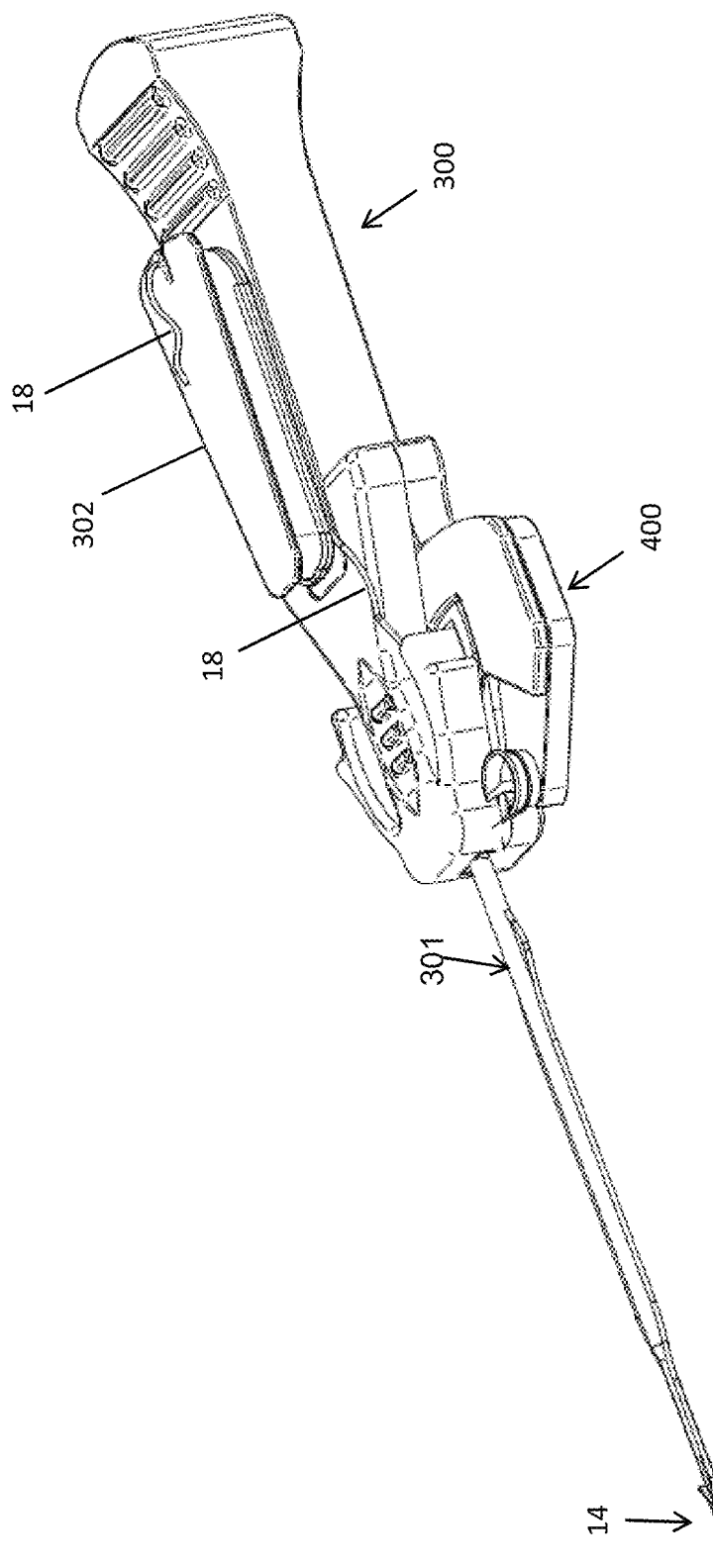
Figure 7A:
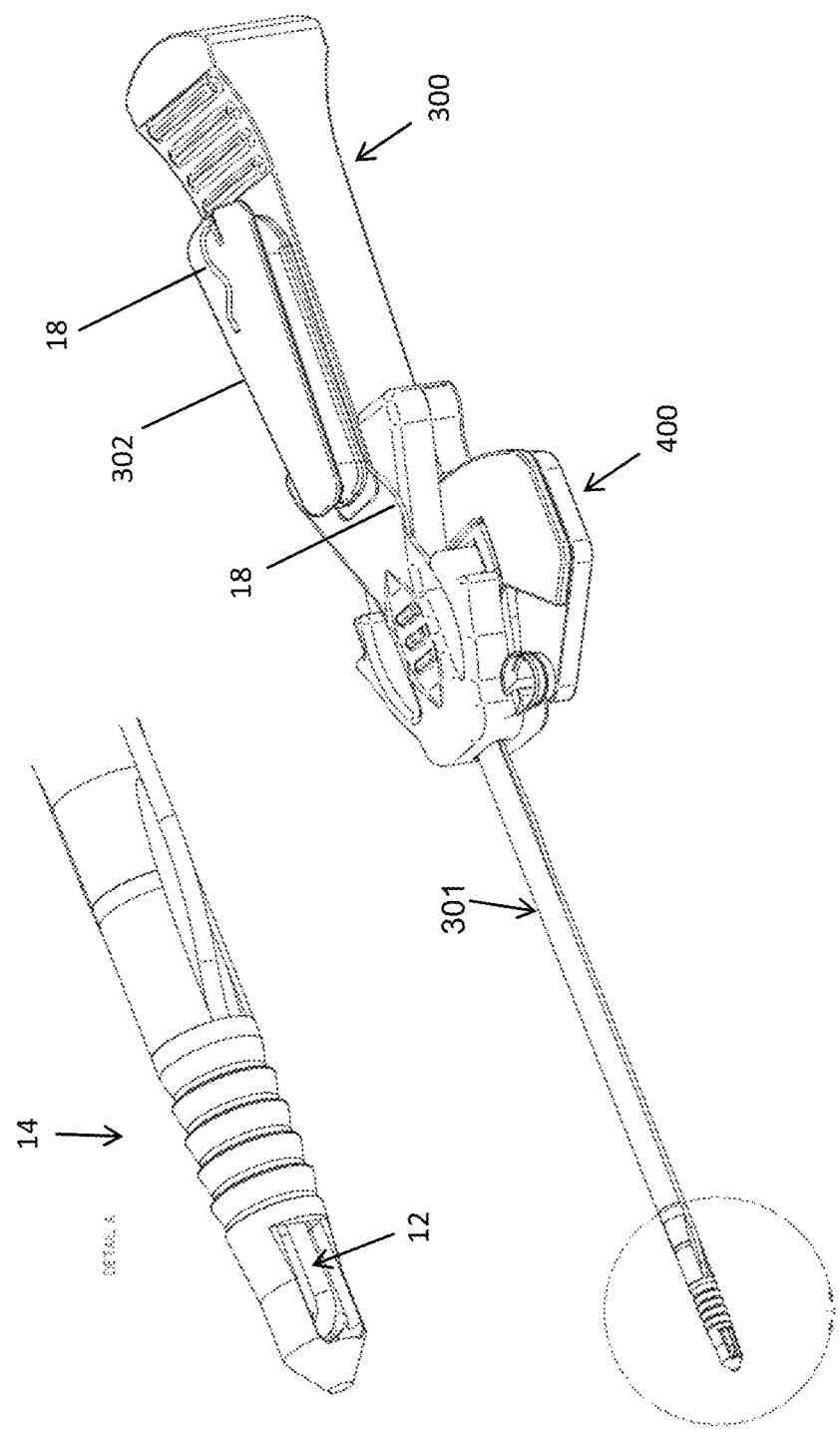
Figure 7B:
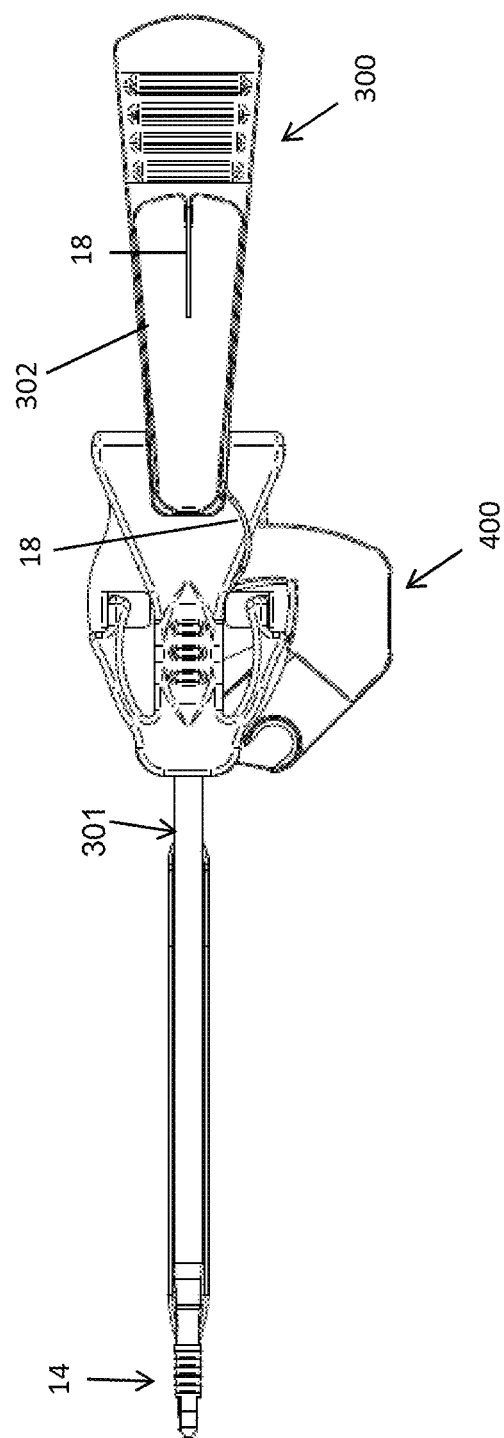
Figure 7C:
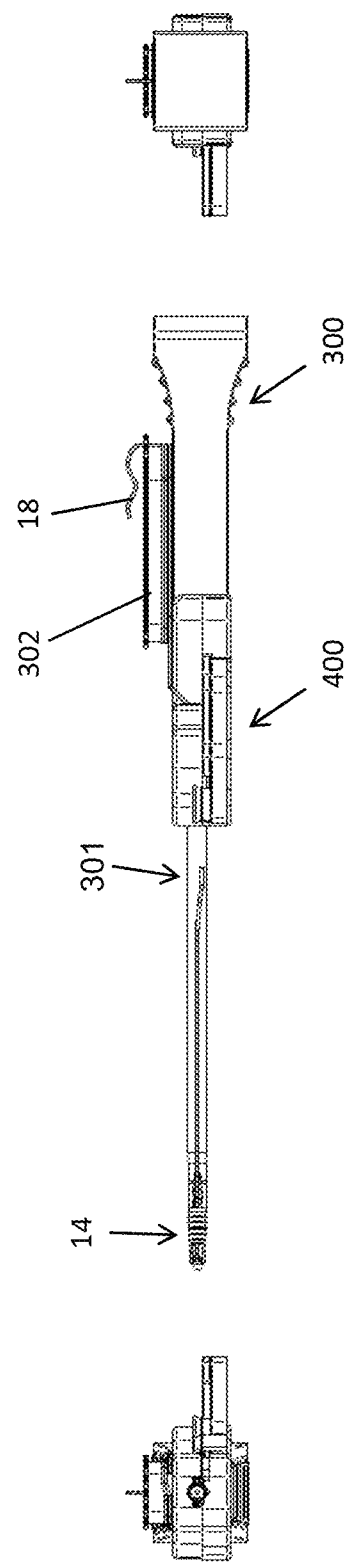
Figure 8:
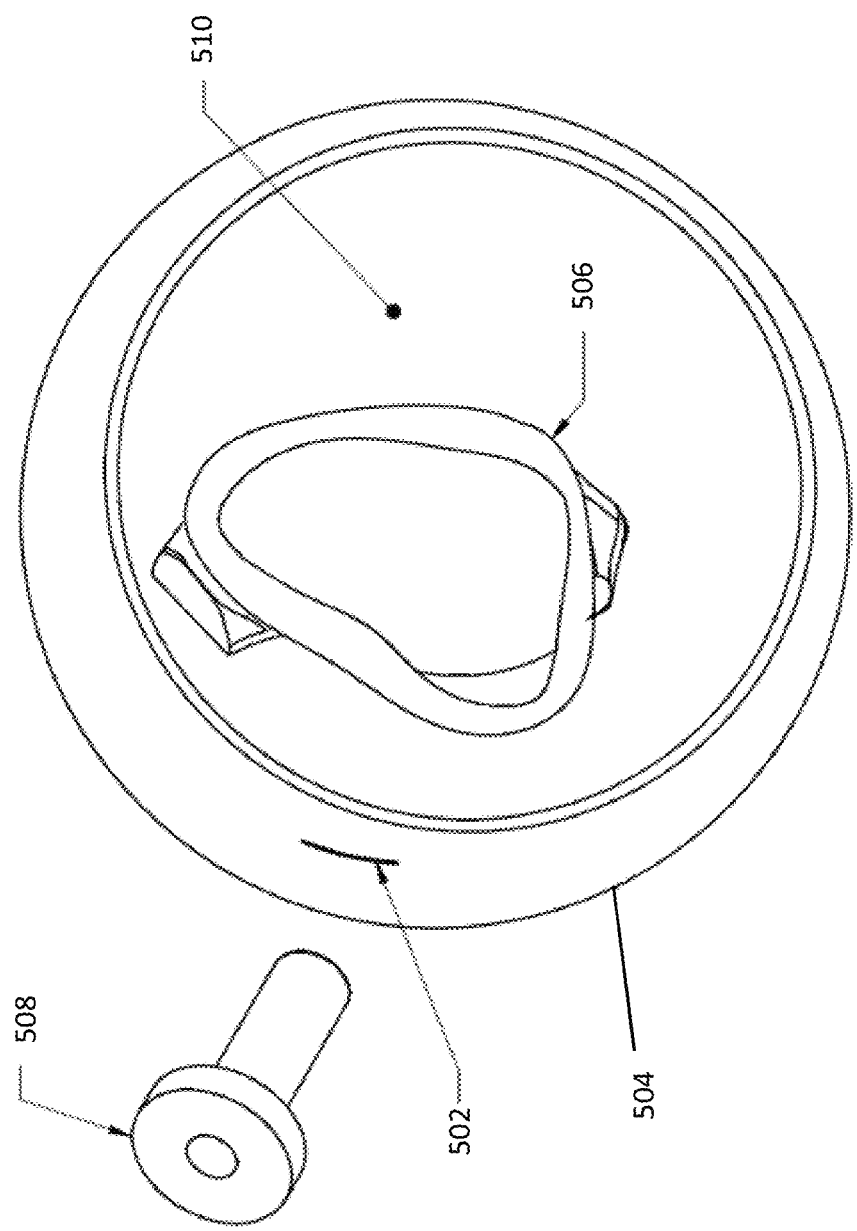
Figure 9:
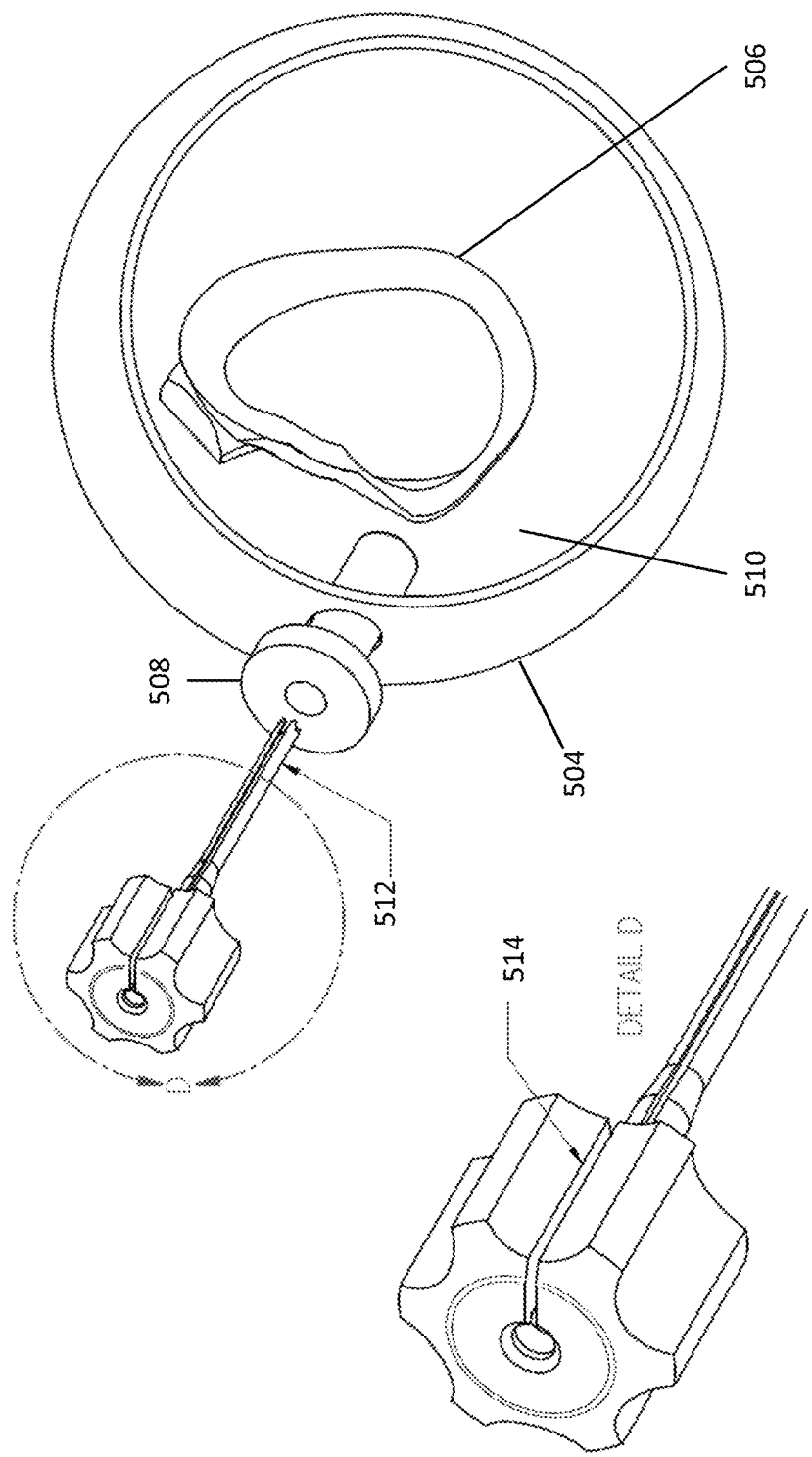
Figure 10:
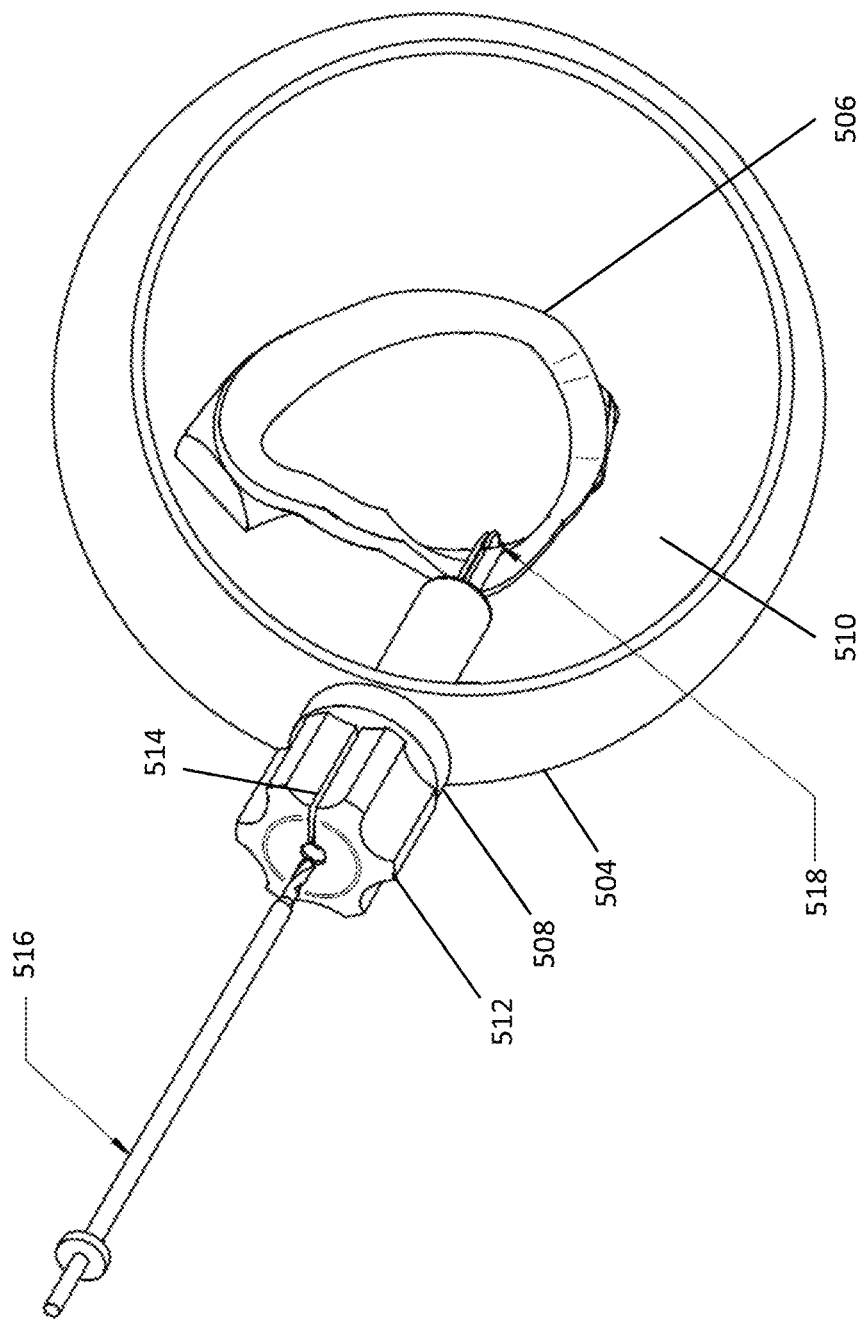
Figure 11:
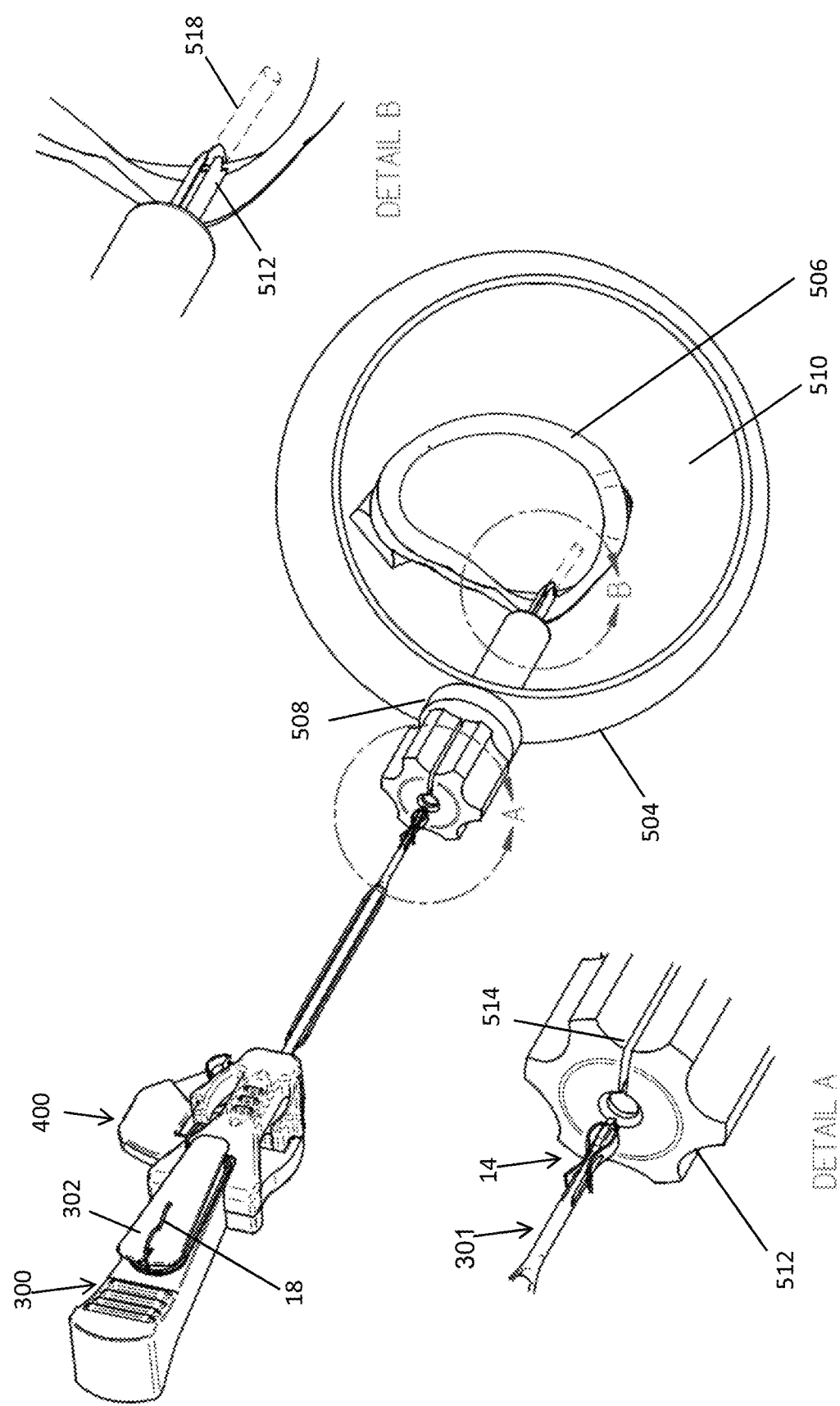
Figure 12:
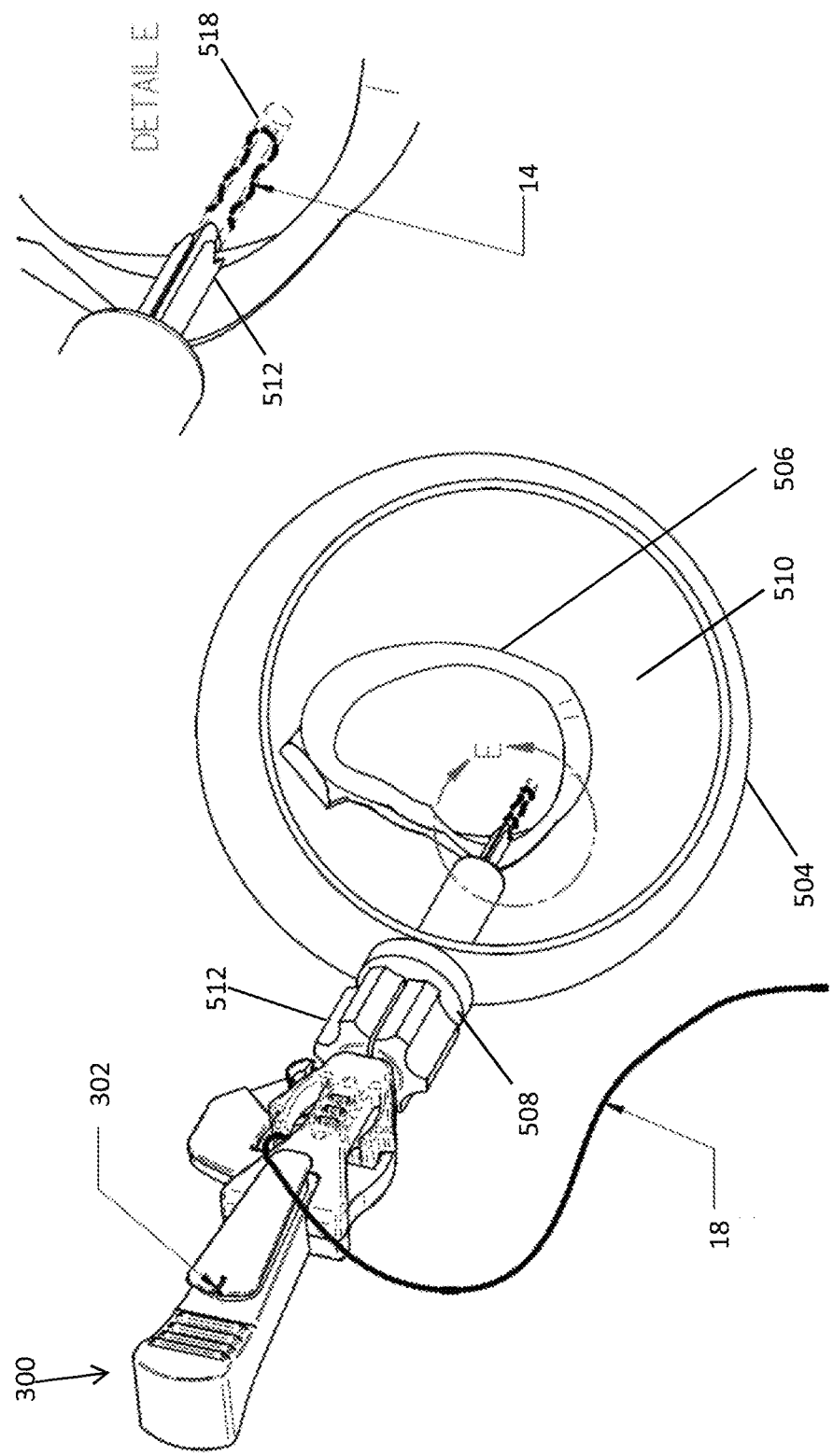
Figure 13:
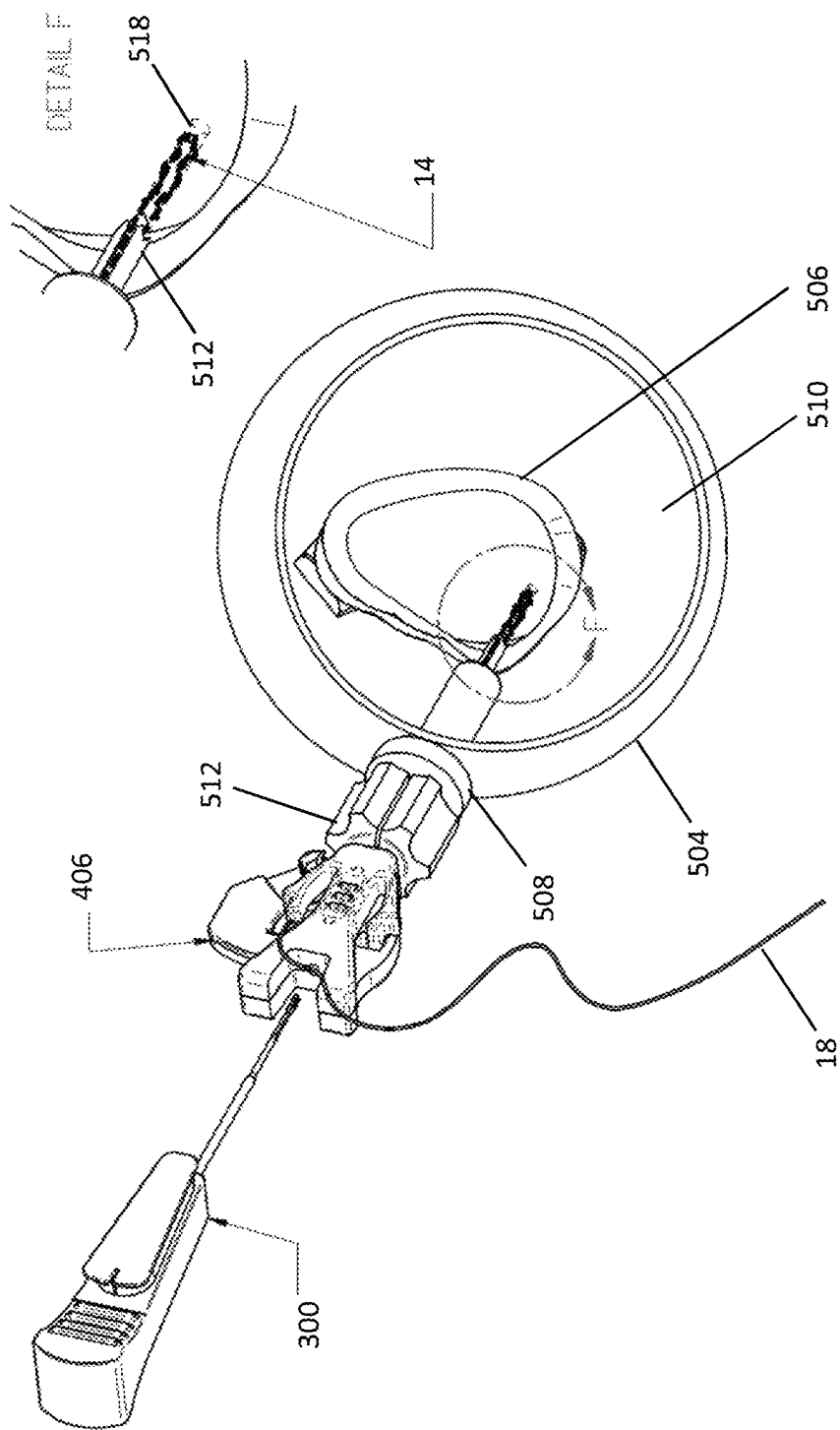
Figure 14:
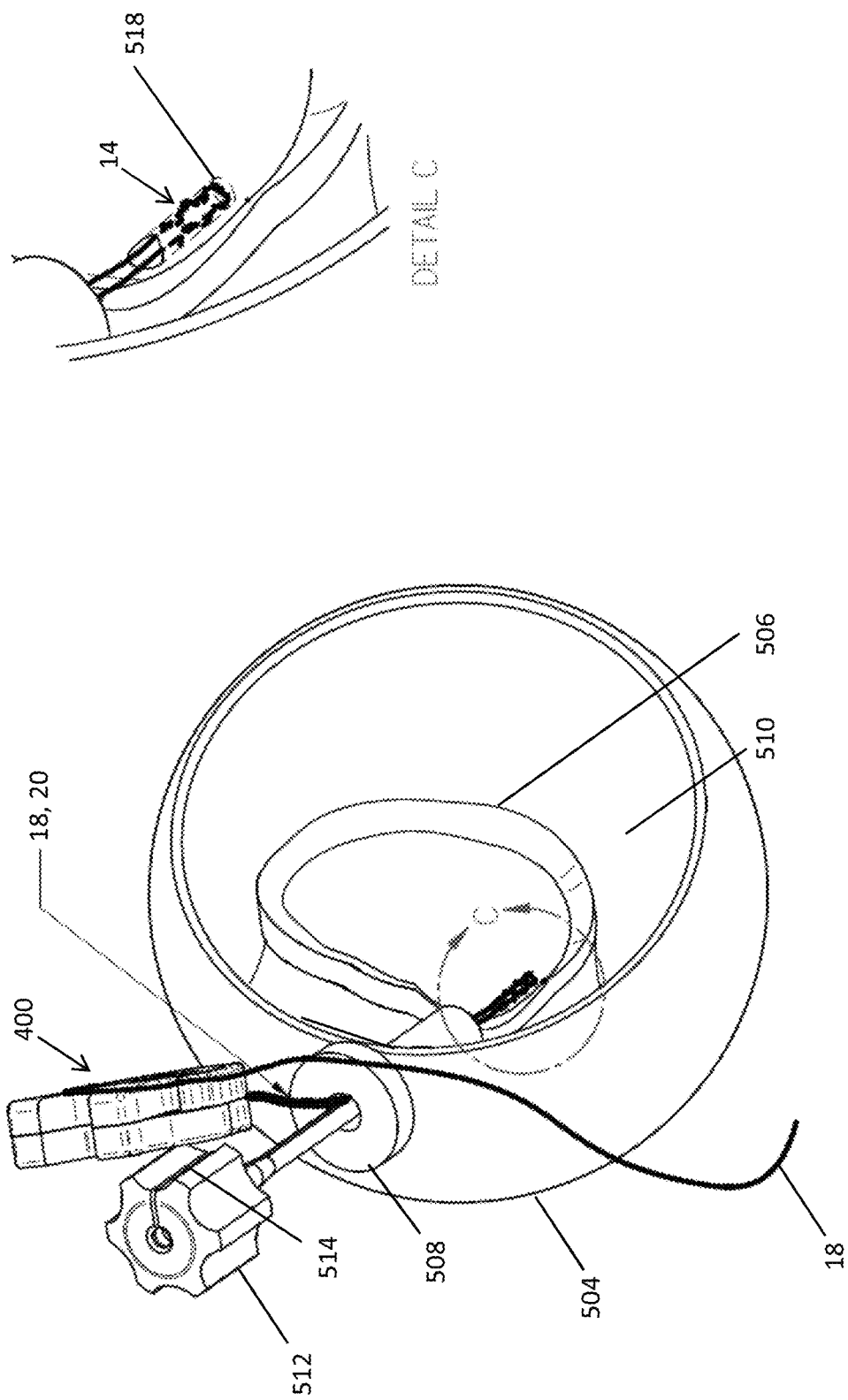
Figure 15:
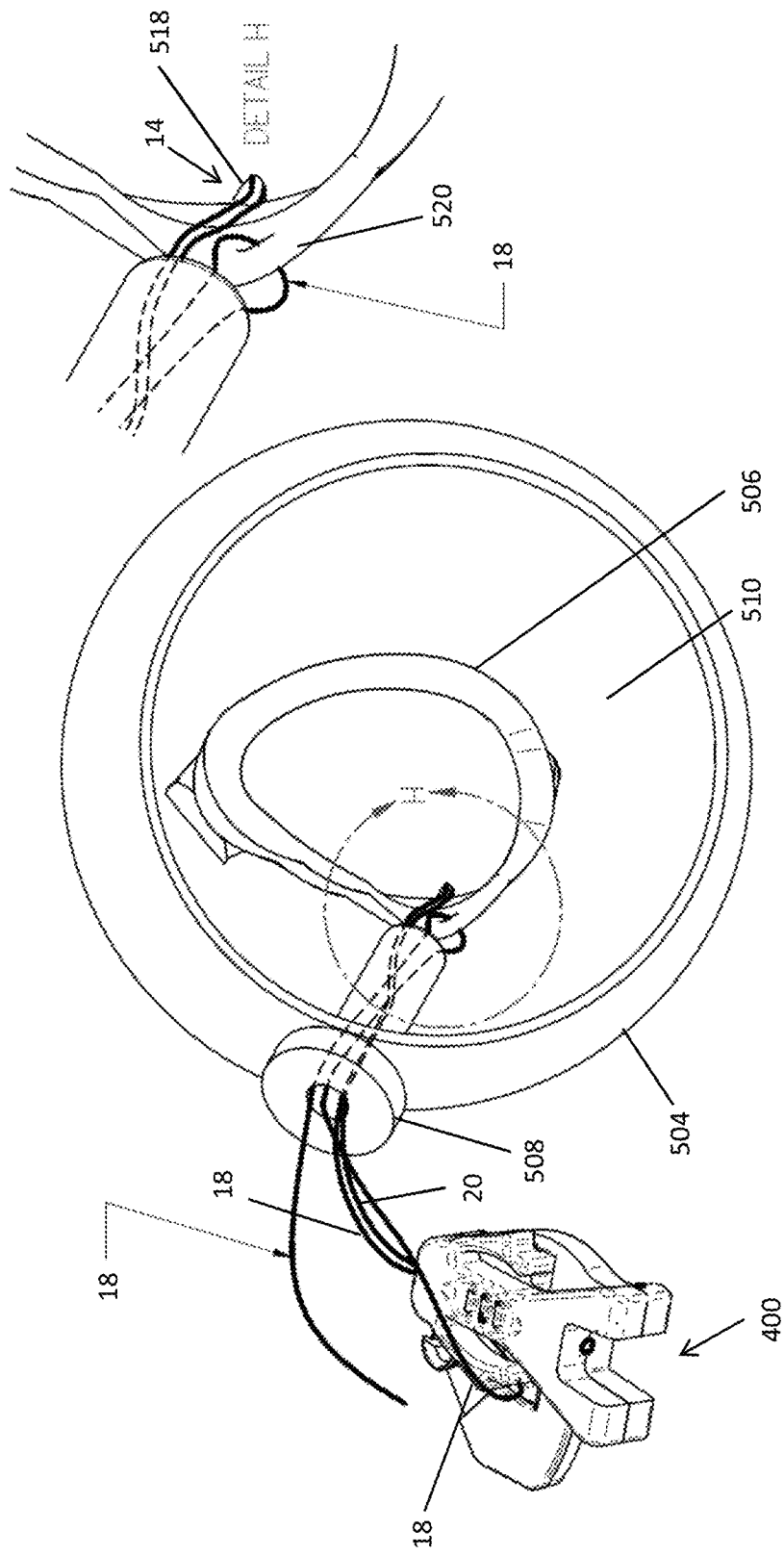
Figure 16:
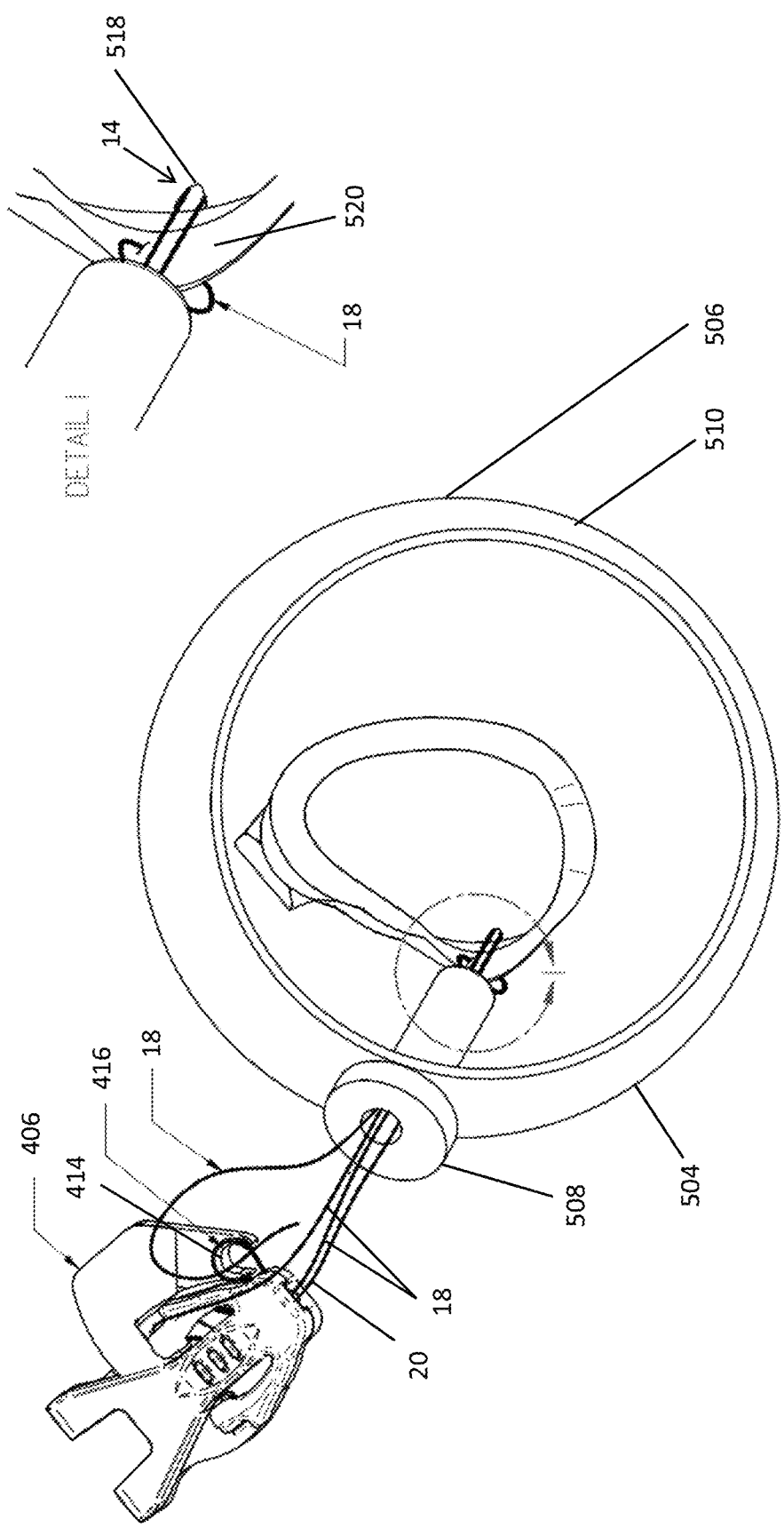
Figure 17:
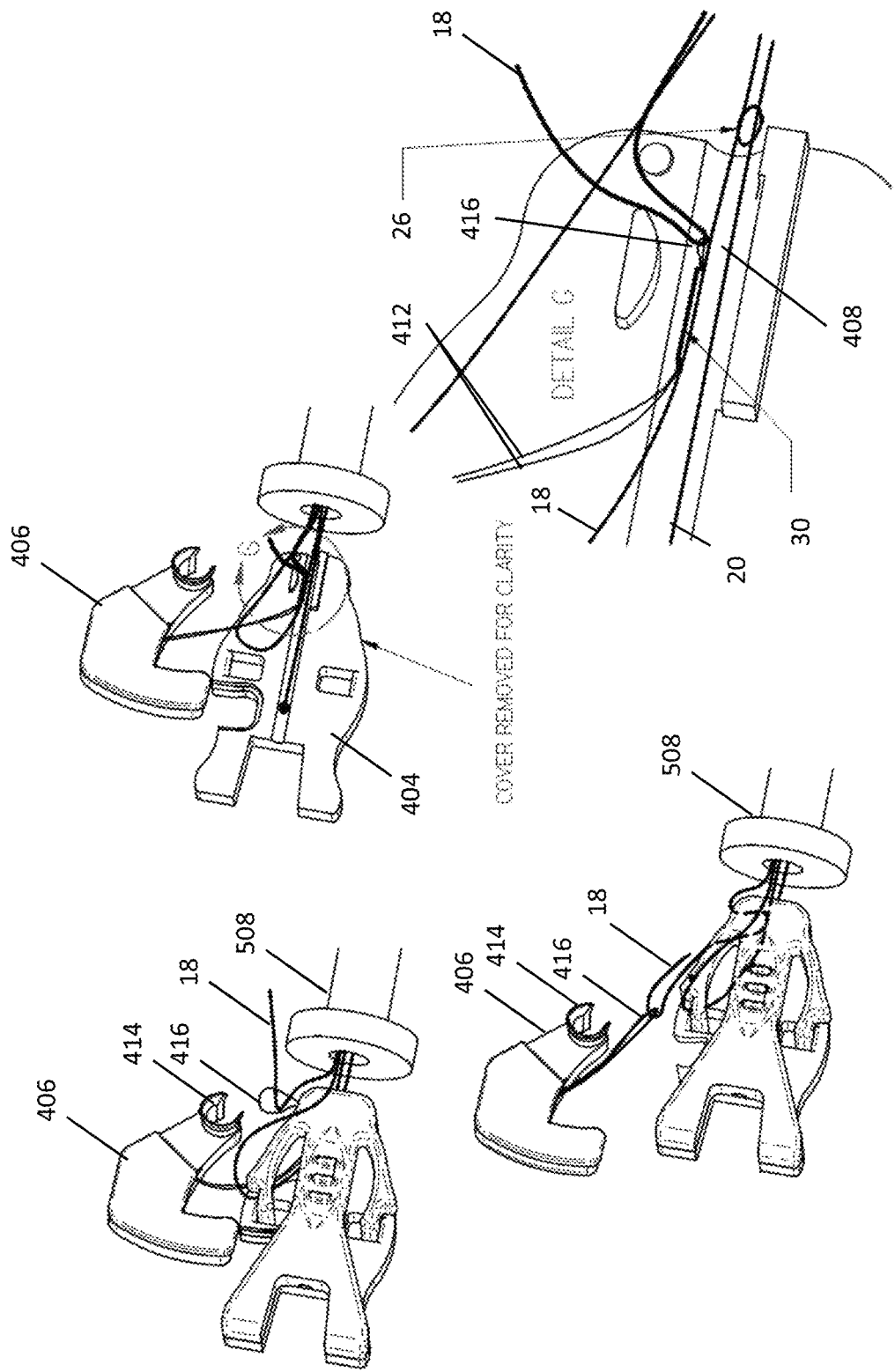
Figure 18:
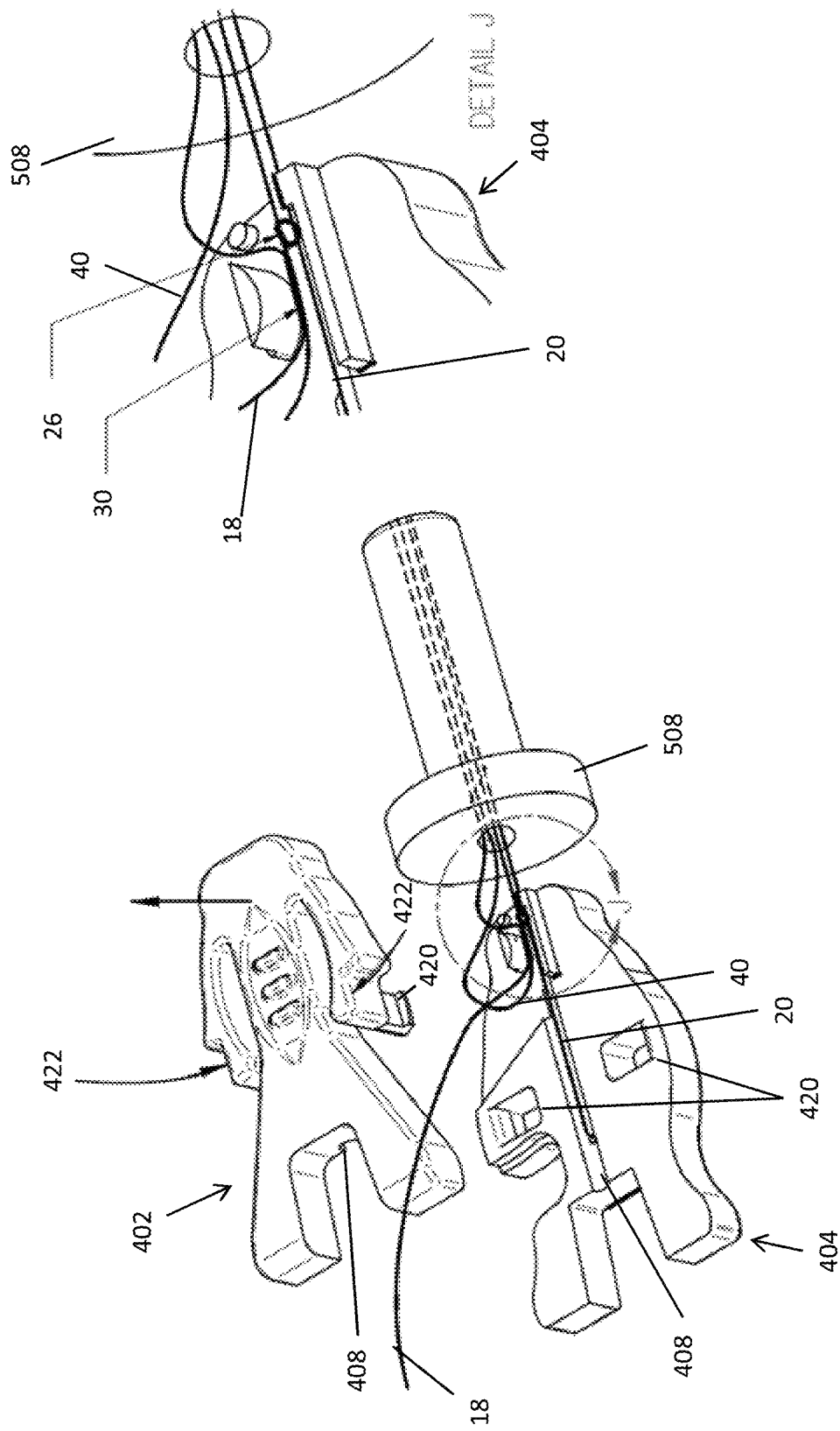
Figure 19:
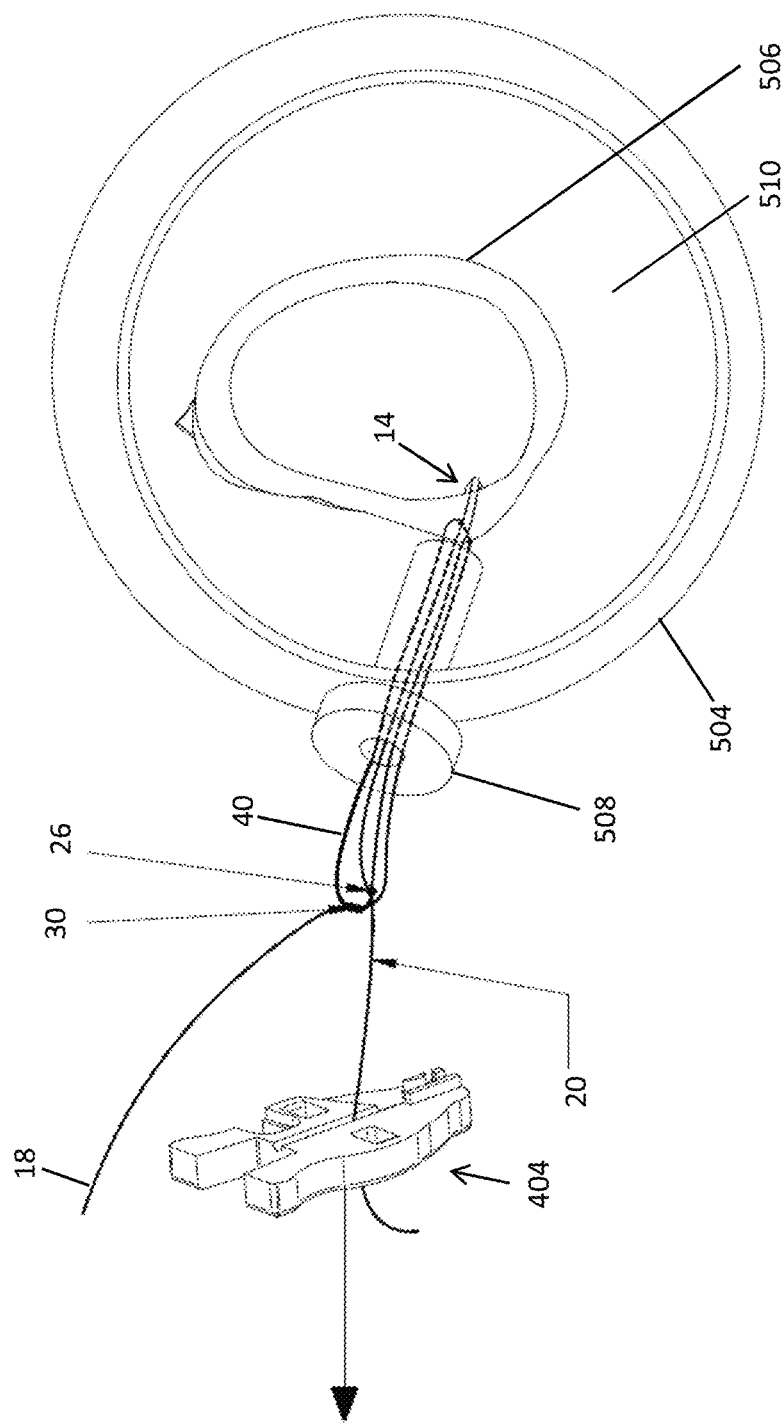
Figure 20:
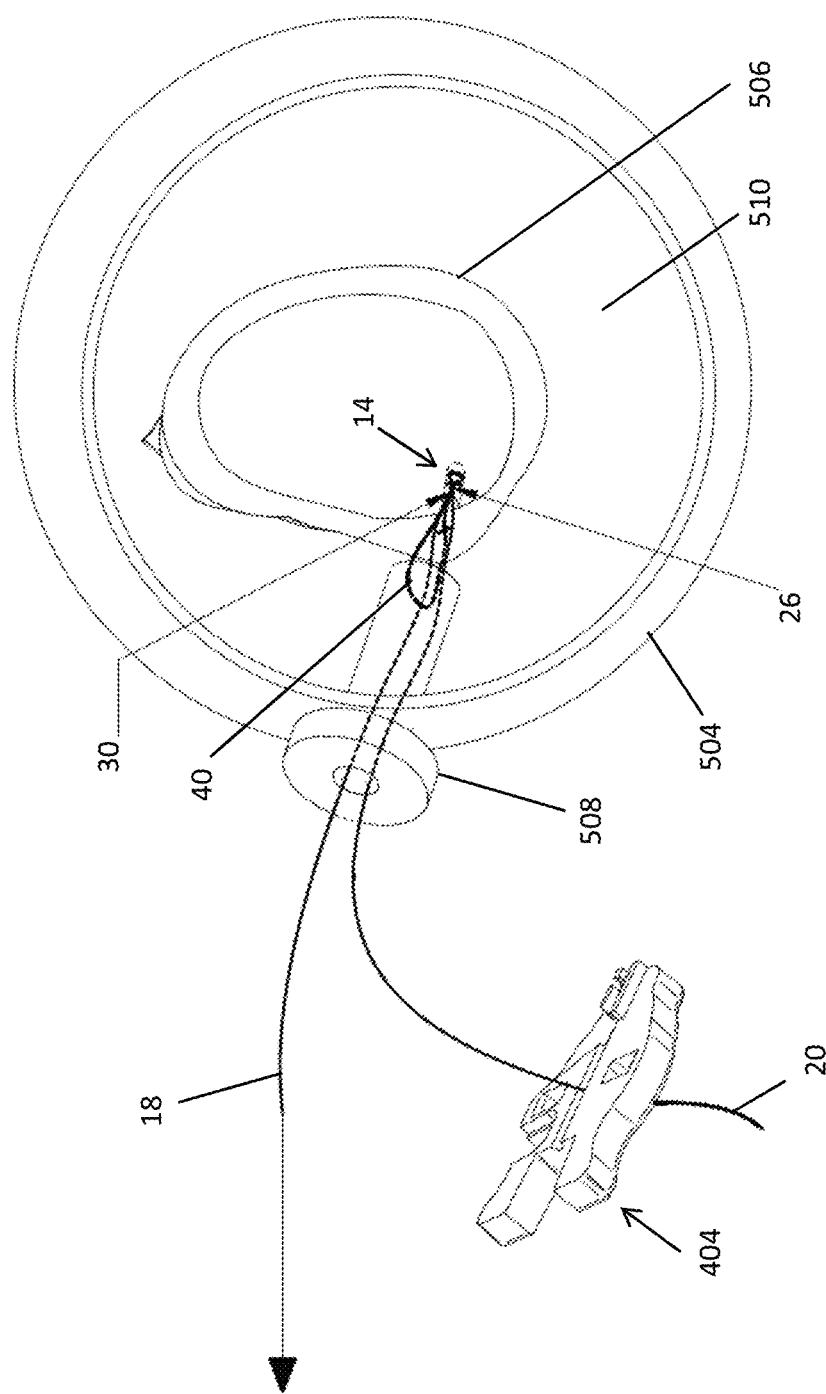
Figure 21:
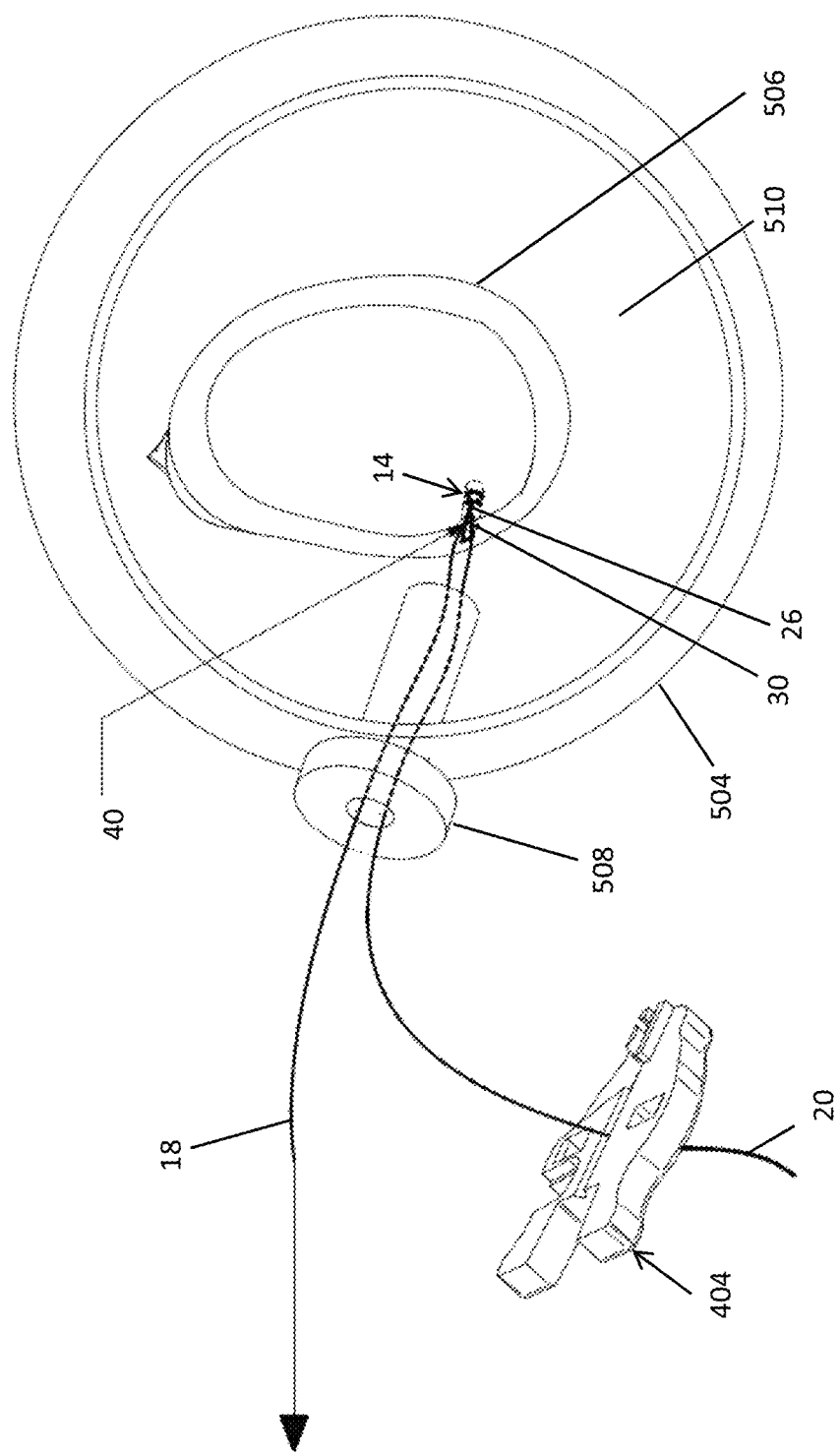
Figure 22:
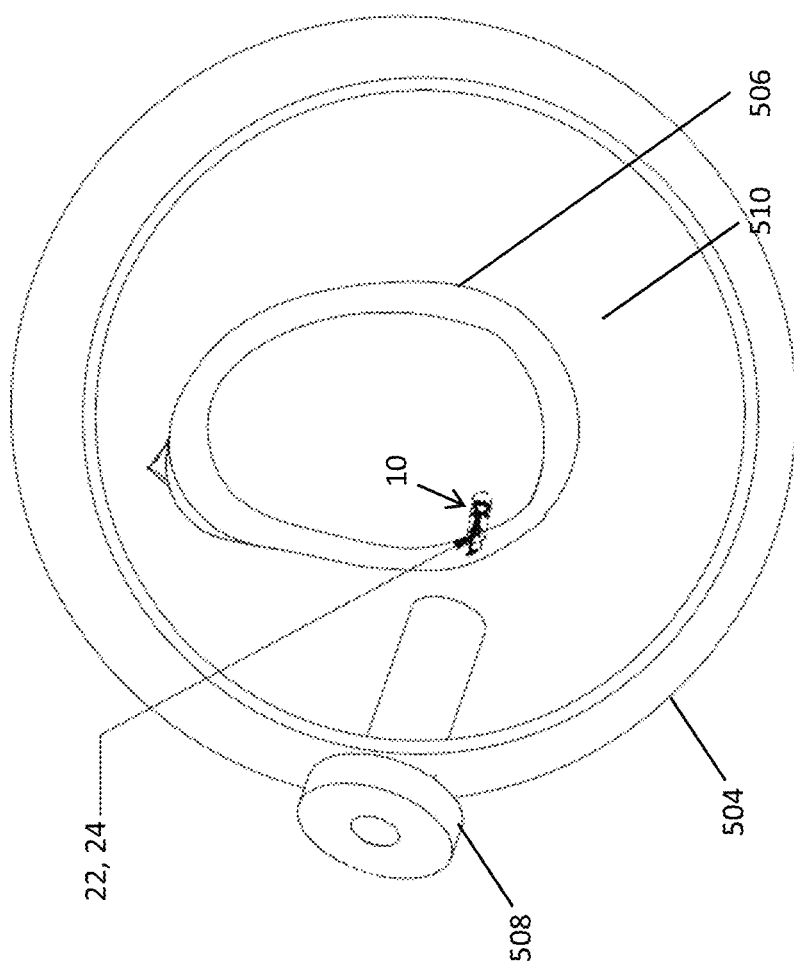

FIG. 4A a perspective view schematic representation of the loop strand at the first step of creating the splice according to an embodiment;

FIG. 4B is a side view schematic representation of the loop strand at the second step of creating the splice according to an embodiment;

FIG. 4C is a side view schematic representation of the loop strand at the third step of creating the splice according to an embodiment;

FIG. 4D is a side view schematic representation of the loop strand at the last step of creating the splice according to an embodiment;

FIG. 4E is a side view schematic representation of the loop strand creating the one-way locking loop according to an embodiment;

FIG. 4F is a side view schematic representation of the one-way locking loop according to an embodiment;

FIG. 5 is a side view schematic representation of the knotless instability suture anchor construct loaded onto a threader assembly according to an embodiment;

FIG. 6 is a perspective view schematic representation of an all-suture anchor loaded on a driver and threader assembly according to an embodiment;

FIG. 7A is a perspective view schematic representation of a rigid suture anchor loaded on a driver and threader assembly according to an embodiment;

FIG. 7B is a top view schematic representation of the rigid suture anchor loaded on a driver and threader assembly of FIG. 7A;

FIG. 7C is a side view schematic representation of the rigid suture anchor loaded on a driver and threader assembly of FIG. 7A;

FIG. 8 is a perspective view schematic representation of a cannula at a surgical site according to an embodiment;

FIG. 9 is a perspective view schematic representation of a drill guide entering the cannula of FIG. 8;

FIG. 10 is a perspective view schematic representation of a drill bit inserted into the drill guide of FIG. 9;

FIG. 11 is a perspective view schematic representation of a driver and threader assembly entering the drill guide of FIG. 9;

FIG. 12 is a perspective view schematic representation of the loop strand of the knotless instability suture anchor construct released from the handle cleat of the driver;

FIG. 13 is a perspective view schematic representation of the driver exiting the drill guide and threader assembly;

FIG. 14 is a perspective view schematic representation of the threader assembly removed from the drill guide;

FIG. 15 is a perspective view schematic representation of the loop strand secured around detached tissue and exiting the cannula;

FIG. 16 is a perspective view schematic representation of the loop strand extending through the threader loop on the threader arm;

FIG. 17 is a perspective view schematic representation of threader arm pulling the loop strand through the splice;

FIG. 18 is a perspective view schematic representation of the cover of the threader assembly released from the back piece;

FIG. 19 is a perspective view schematic representation of pulling the post strand by pulling the back piece in a direction distal the cannula to reduce the size of the positioning loop;

FIG. 20 is a perspective view schematic representation of pulling the loop strand to reduce the size of the locking loop;

FIG. 21 is a perspective view schematic representation of the tissue in apposition to the bone when the locking loop is minimized; and FIG. 22 is a perspective view schematic representation of the trimmed ends of the knotless instability suture anchor construct.

DETAILED DESCRIPTION OF THE INVENTION

Figure 1:
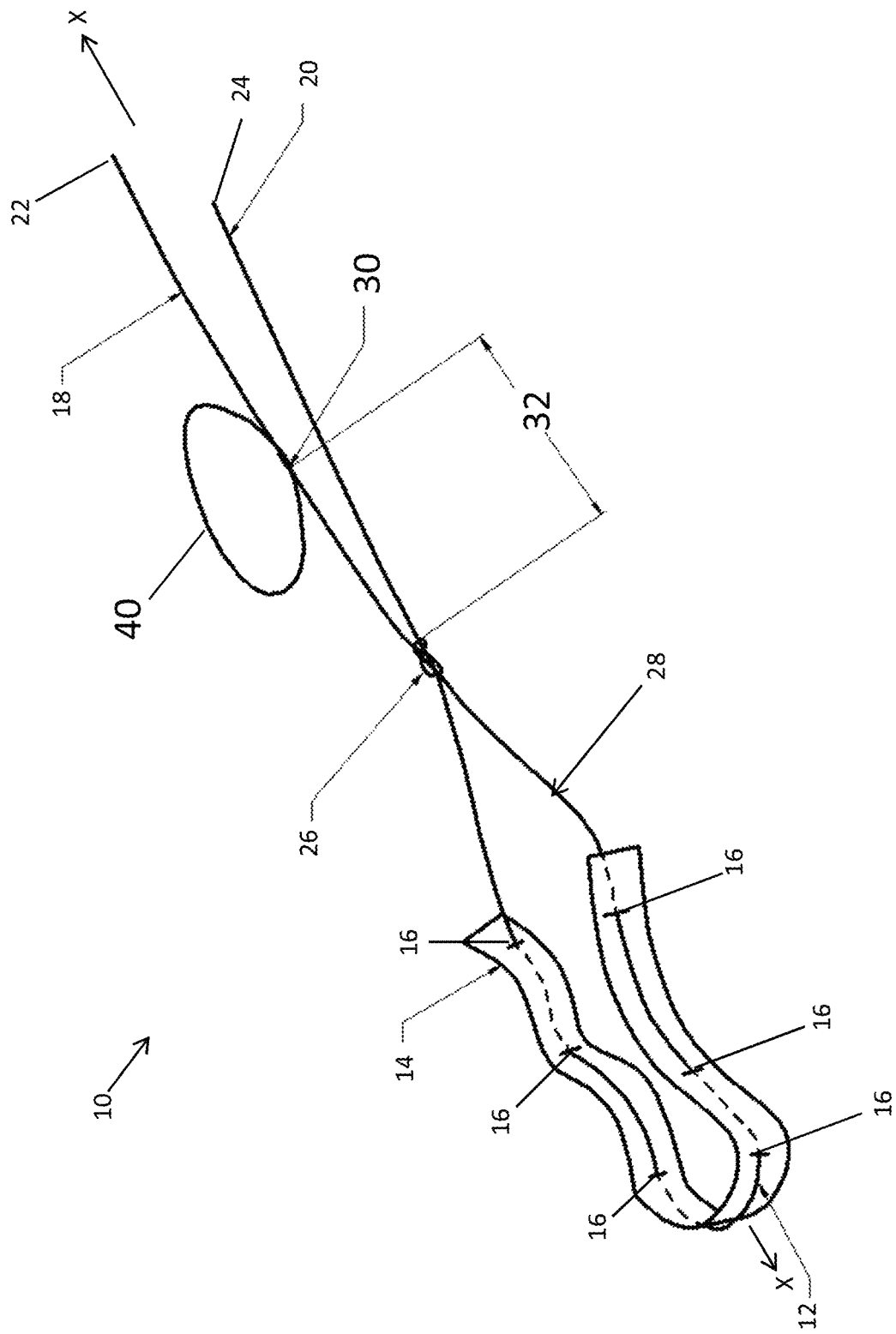
FIG. 1 is a perspective view schematic representation of knotless instability suture anchor construct according to an embodiment.

Referring now to the drawings, wherein like reference numerals refer to like parts throughout, there is seen in FIG. 1 an illustrative embodiment of the knotless instability suture anchor construct 10. The construct 10 comprises a length of suture 12 woven through an anchor 14 or other fixation device. As shown in the depicted embodiment, the anchor 14 is a strip of rectangular suture material forming an all-suture anchor with suture 12 (as should be understood by a person of ordinary skill in the art in conjunction with a review of the disclosure including, but not limited to, embodiments of an all suture anchor shown and described in US 20210290004, the disclosure of which is incorporated by reference herein in its entirety). Specifically, the anchor 14 can be comprised of flat soft woven material, like Dyneema, for example. The anchor 14 is composed of soft material, for example, in order to prevent damage to the surrounding tissue if the construct 10 moves within the body.

In the depicted embodiment, the length of suture 12 is woven through the anchor 14 such that the length of suture 12 enters and exits the anchor 14 at six apertures 16 along the anchor 14. Weaving the length of suture 12 through the anchor 14 at six apertures 16 is especially beneficial (although any number of apertures can be used as may be appropriate to meet the desired functionality of the suture construct 10) when the anchor 14 is an all-suture anchor because there is sufficient tension to deploy and expand the anchor 14 without risking the length of suture 12 pulling through the space between numerous apertures 16 in close proximity. Other configurations and similar suture anchors can be applied to the construct 10 while remaining within the spirit and scope of embodiments of the present invention.

Still referring to FIG. 1, the length of suture 12 has a loop strand 18 and a post strand 20, with the anchor 14 woven therebetween. In other words, when the length of suture 12 is folded in half, the loop strand 18 and the post strand 20 extend proximal from the anchor 14, as shown in FIG. 1. The loop strand 18 terminates at a first end 22 and the post strand 20 terminates at a second end 24. In the depicted embodiment, the loop strand 18 and the post strand 20 form a sliding construct 26 between the anchor 14 and the first and second ends 22, 24. Formation of the sliding construct 26 creates a positioning loop 28 with a perimeter defined at least in part by the length of suture 12 woven through the anchor 14.

Figure 2A:
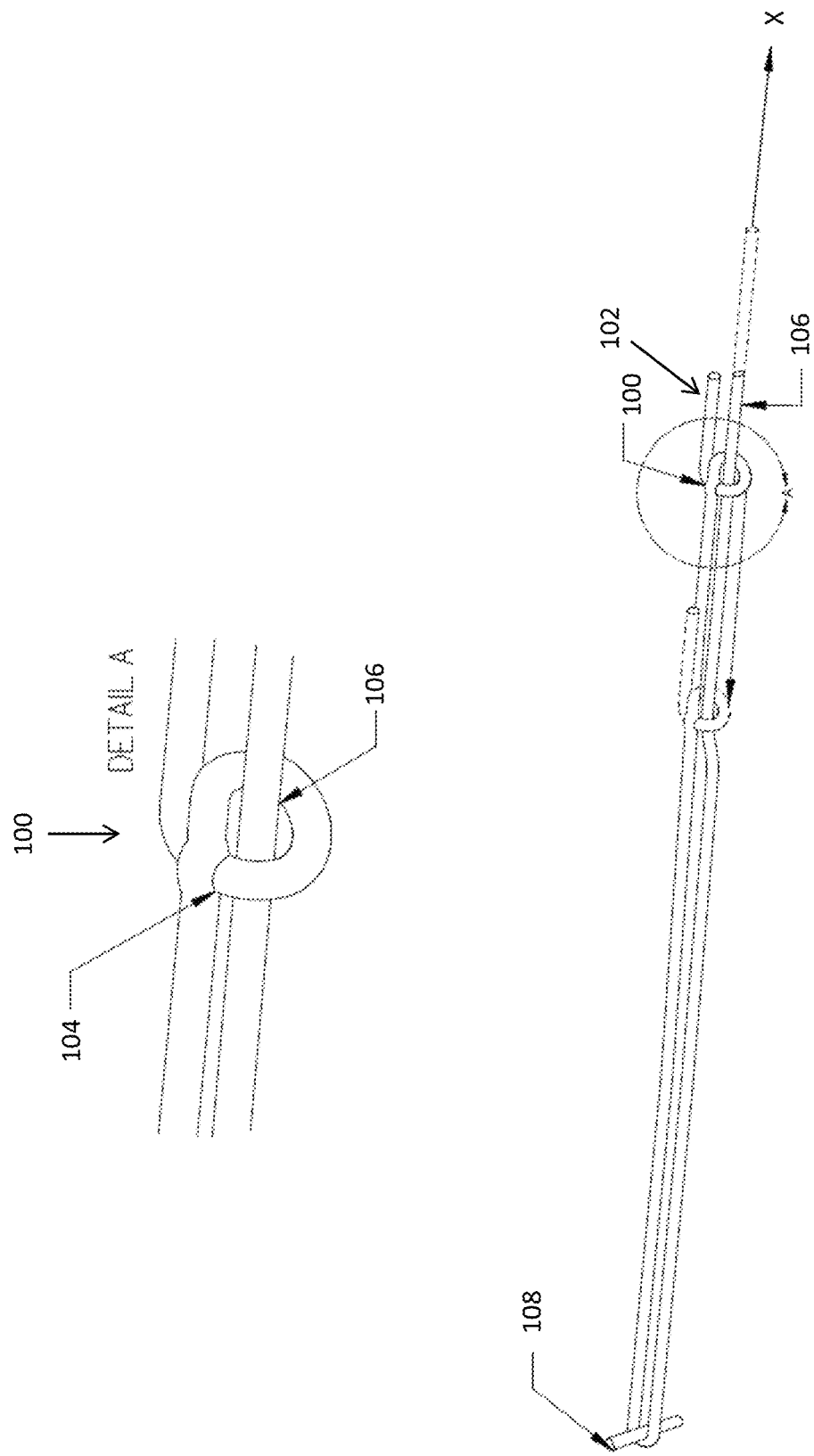
FIG. 2A is a perspective view schematic representation of a single friction hitch according to an embodiment.
Figure 2B:
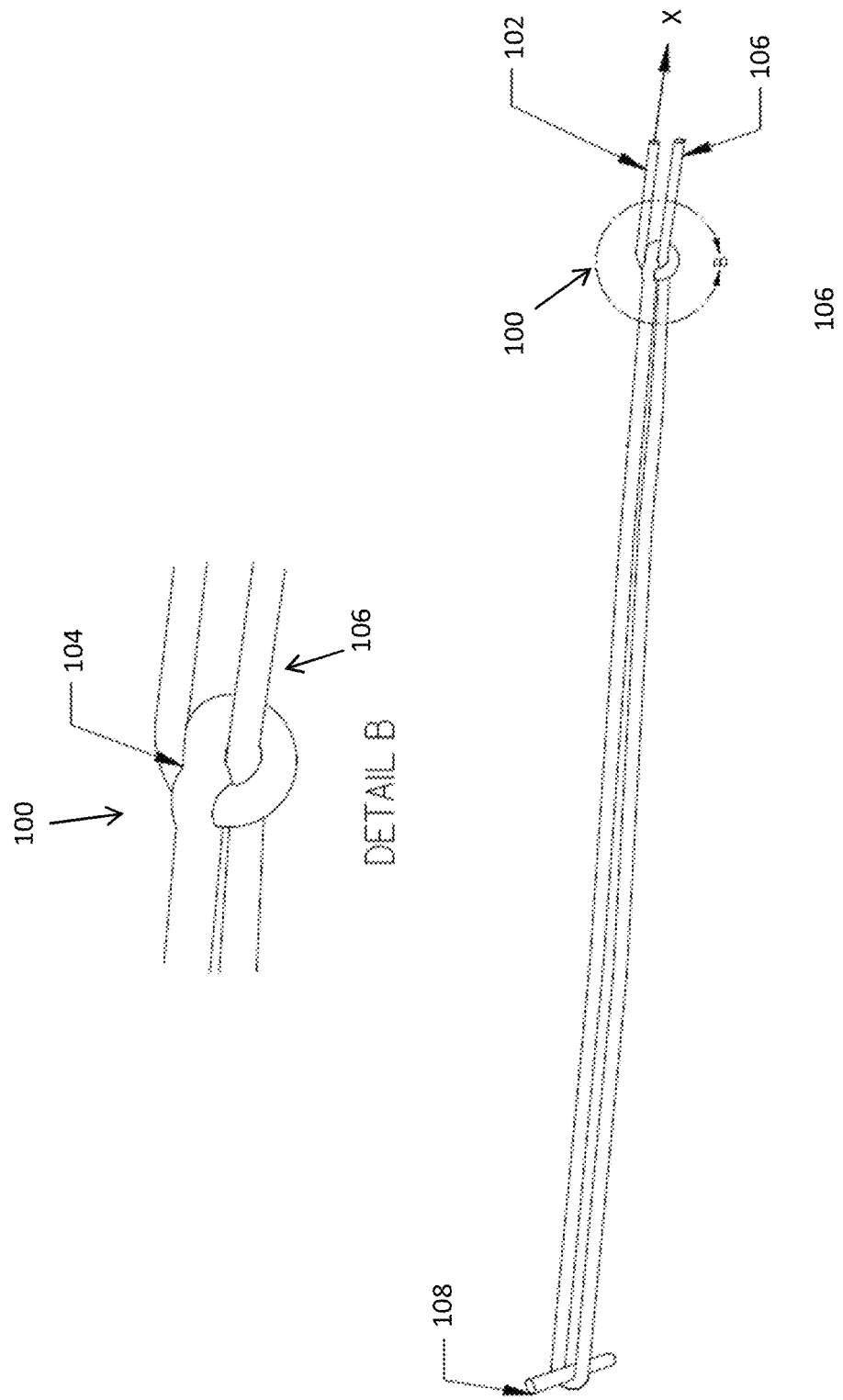
FIG. 2B is another perspective view schematic representation of the single friction hitch of FIG. 2A.
Figure 3:
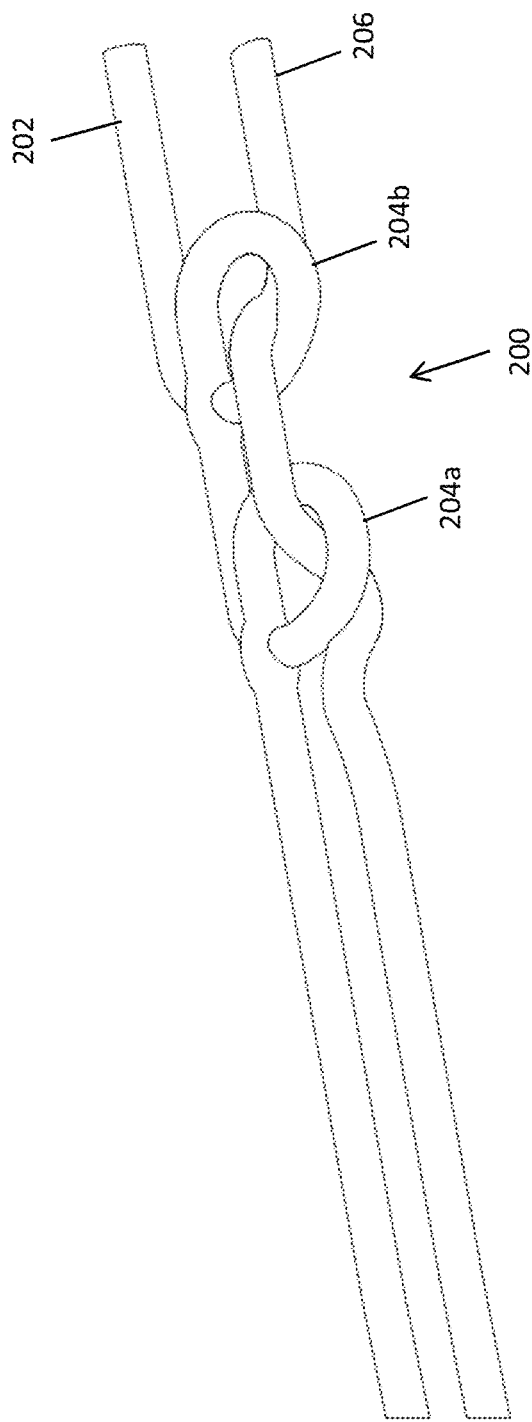
FIG. 3 is a perspective view schematic representation of a multiple friction hitch according to an embodiment.

Turning briefly to FIGS. 2A-3, there are shown schematic representations of multiple embodiments of the sliding construct 26. In FIGS. 2A-2B, the sliding construct 26 is shown as a single friction hitch 100. In the single friction hitch 100 embodiment, a loop strand 102 is passed through itself to create a friction hitch loop 104. Then, the post strand 106 is passed through the friction hitch loop 104. In the depicted embodiment, the post 108 functions as an anchor 14 (shown in FIG. 1) in a bone hole. Applying traction to the post 108 causes the friction hitch 100 to slide along the post strand 106, as shown in FIG. 2A. Next, turning to FIG. 2B, when traction is applied to the loop strand 102, the friction hitch loop 104 tightens and reduces its perimeter around the post strand 106 to prevent sliding.

In FIG. 3, there is shown a schematic representation of an embodiment wherein the sliding construct 26 is a multiple friction hitch 200. In the depicted embodiment, the loop strand 202 is passed through itself at two separate locations and the post strand 206 is passed through the two loops 204a, 204b of the multiple friction hitch 200. In alternative embodiments of the multiple friction hitch 200, any plurality of loops may be utilized. Having at least two loops 204a, 204b of the multiple friction hitch 200 improves security over the single friction hitch 100.

Referring back to FIG. 1, the construct 10 further comprises a splice 30 in the loop strand 18. As shown in FIG. 1, the splice 30 is located along the loop strand 18 between the sliding construct 26 and the first end 22. The splice 30 is at a fixed distance (in length of suture 12) from the sliding construct 26. Stated differently, the gap 32 in the loop strand 18 that extends between the splice 30 and the sliding construct 26 is a fixed length. In many embodiments, the splice 30 is no farther than 1-2 mm immediately proximal the sliding construct 26.

Turning to FIGS. 4A-4F, there are shown schematic representations of the steps to create the splice 30 in the loop strand 18. Formation of the splice 30 begins by bending the first end 22 of the loop strand 18 distally 180° backward (or counterclockwise) toward the remainder of the loop strand 18, as shown in FIG. 4A. Then, as shown in FIG. 4B, the first end 22 is passed through the loop strand 18 at an aperture 34 created perpendicular to the x-axis of the remainder of the loop strand 18. Next, according to FIG. 4C, the first end 22 is pulled proximally such that the first end 22 extends along the x-axis of the remainder of the loop strand 18, completing a 360° counterclockwise turn. The resulting splice 30, shown in FIGS. 4C and 4D, has a reinforced area 36 created immediately proximal to the sliding construct 26 (shown in FIG. 1). The reinforced area 36 is an inverted suture portion proximal to the aperture 34.

To create a one-way splice or locking loop 40 in the splice 30, the first end 22 is passed through the aperture 34 of the splice 30 in a clockwise fashion, as shown in FIG. 4E. Turning to FIG. 4F, the first end 22 then enters the loop strand 18 and continues proximally along the x-axis of the remainder of the loop strand 18 for 5-10 mm before exiting the loop strand 18 at a second aperture 38 to complete a one-way locking loop 40 (also shown in FIG. 1). As later described and shown in FIGS. 15-18, the first end 22 can be passed through the splice 30 using a threader assembly to complete the one-way locking loop 40. Therefore, once the construct 10 has been formed as shown and described in FIGS. 1-4D, the construct 10 can be loaded onto a threader assembly and driver to facilitate deployment of the construct 10 in a bone.

Referring now to FIGS. 5-7C, there are shown embodiments of various anchors 14 of the construct 10 loaded onto a driver 300 (which includes a drive shaft 301) and a threader assembly 400. First, as shown in FIG. 5, the construct 10 is loaded onto the threader assembly 400. The threader assembly 400 comprises a cover 402 and a back piece 404 with a removable threader arm 406. In the depicted embodiment, the construct 10 is loaded into a channel 408 in the threader assembly 400 through both the back piece 404 and the cover 402. The post strand 20 is fed through an aperture 410 in the channel 408 and tied in a knot on the opposing side of the back piece 404. A strand of threader material 412 is looped around a raised hook 414 on the threader arm 406. The hook 414 on the threader arm 406 is rounded to create a threader loop 416 when threader material 412 is wrapped therearound. The ends 418 of the threader material 412 are fed through the splice 30. The cover 402 is then secured on back piece 404 by a pair of movable clips 420. Squeezing tabs 422 on the cover 402 move the clips 420 closer to each other to fit into clip receiving apertures 424 on the back piece 404.

In FIG. 6, the anchor 14 shown is an all-suture anchor loaded on the driver 300 in the threader assembly 400. As depicted, the anchor 14 is loaded on a driver 300 which extends through the threader assembly 400 via the channel 408. The loop strand 18 is pulled between the cover 402 and the back piece 404, and is wrapped around a handle cleat 302 on the driver 300. By wrapping the loop strand 18 around the handle cleat 302, the anchor 14 remains secured on the driver 300 when the anchor 14 is inserted into a bone hole. In FIGS. 7A-7C, there are shown perspective, top, and side views of a rigid anchor 14 with suture 12 threaded therethrough and similarly loaded on the driver 300 coupled to the threader assembly 400.

Referring now to FIGS. 8-22, there are shown schematic representations of steps of a method for securing tissue to bone using the knotless instability suture anchor construct 10 according to a first embodiment. Prior to utilizing the knotless instability suture anchor construct 10, the surgical area 500 is prepared. Referring to FIG. 8, an incision 502 is made through the skin 504 distal the bone 506. In the depicted embodiment, the bone 506 is a labrum with a detachment injury. Next, a cannula 508 is inserted through the incision 502 and into the joint space 510 surrounding the bone 506.

Thereafter, as shown in FIG. 9, a drill guide 512 is inserted through the cannula 508 and placed in position against the bone 506. In the depicted embodiment, the drill guide 512 comprises a slot 514 to facilitate removal of the loop strand 18 (not shown) through the slot 514 during a subsequent step. Then, as shown in FIG. 10, a drill bit 516 is inserted through the drill guide 512 to create a bone hole 518. Next, the drill bit 516 is removed and the anchor 14 is inserted into the bone hole 518 with the threader assembly 400 and the driver 300, as depicted in FIG. 11. As shown, the embodiment of the knotless instability suture anchor construct 10 is preloaded onto the threader assembly 400 and drill guide 300 (also shown in FIGS. 5-7C).

Thereafter, the driver 300 pushes the anchor 14 into the bone hole 518, as shown in FIG. 12, and the loop strand 18 is then removed from the handle cleat 302. Referring now to FIG. 13, the driver 300 is removed and the threader assembly 400 remains engaged with the drill guide 512. Next, as shown in FIG. 14, the threader assembly 400 is removed from the drill guide 512. To do so, the loop strand 18 and the post strand 20 are pulled through the slot 514 in the drill guide 512 to disengage the threader assembly 400 from the drill guide 512. Then, the drill guide 512 is pulled out of the cannula 508.

Referring to FIG. 15, the loop strand 18 is passed through the cannula 508 around or through the detached tissue 520 and back out of the cannula 508 using a shuttle or other suture passing instrument. Next, the loop strand 18 is passed through the threader loop 416 that is wrapped around the raised hook 414 of the threader assembly 400, as shown in FIG. 16.

At the next step, shown in FIG. 17, the threader arm 406 is pulled to pass the loop strand 18 through the splice 30 and complete the one-way locking loop 40. Then, tabs 422 on the cover 402 of the threader assembly 400 are squeezed to release the cover 402 from the back piece 404. As the tabs 422 are compressed inward, the clips 420 move inward and align with the clip receiving apertures 420 on the back piece 404. Once aligned with the clip receiving apertures 420, the clips 420 can be pulled upward causing the cover 402 to release from the back piece 404. Thereafter, the cover 402 can be pulled up and away from the threader assembly 400, as shown in FIG. 18.

At the next step, shown in FIG. 19, the post strand 20 is pulled by pulling the back piece 404 away from the surgical area 500, which shortens the positioning loop 28 between the anchor 14 and the sliding construct 26. As the perimeter of the positioning loop 28 is reduced, the locking loop 40 is pulled closer to the positioning loop 28 due to the fixed gap 32 between the sliding construct 26 and the splice 30. The post strand 20 is pulled until the perimeter of positioning loop 28 is reduced and the sliding construct 26 is in close proximity to the anchor 14, as shown in FIG. 20. Further, reducing the perimeter of the positioning loop 28 with tension causes the anchor 14 to expand and/or otherwise lock in place within the bone hole 518 (as should be understood by a person of ordinary skill in the art in conjunction with a review of this disclosure).

Finally, as shown in FIG. 21, the perimeter of the locking loop 40 around the tissue 520 is reduced by pulling the loop strand 18. Pulling the loop strand 18 tensions the locking loop 40 and holds the tissue 520 in a desired position relative to the anchor 14. The first end 22 and the second end 24 of the construct 10 can be trimmed, as depicted in FIG. 22.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A knotless instability suture anchor construct, comprising:
   an anchor having a length of suture material passing therethrough, the suture material having a loop strand having a central longitudinal axis extending along the length thereof from a first end to a second end thereof and terminating at the first end and a post strand terminating at the second end;
   a splice loop formed by the first end, wherein the splice loop is formed by a length of the loop strand extending into an interior of the loop strand through a first aperture, the length of the loop strand extending parallel to and coaxially along the central longitudinal axis and along the length of the loop strand while within the interior of the loop strand, and extending back outside of the interior of the loop strand through a second aperture, wherein the first and second aperture are on the same side of the loop strand;
   a sliding construct formed by the first end and the second end;
   wherein the sliding construct is configured to adjust the relative position of the splice loop and the anchor.

2. The suture construct of claim 1, further comprising a fixed gap between the splice loop and the sliding construct.

3. The suture construct of claim 1, wherein the sliding construct is positioned distally to the splice loop.

4. The suture construct of claim 1, wherein the sliding construct is selected from the group consisting of a single friction hitch and a multiple friction hitch.

5. The suture construct of claim 1, wherein the loop strand is configured to be pulled to decrease the perimeter of the splice loop from a first size to a second size smaller than the first size.

6. The suture construct of claim 1, wherein the anchor is selected from the group consisting of an all-suture anchor and a rigid anchor.

7. The suture construct of claim 1, wherein the sliding construct creates a positioning loop in the suture material of a first size defined at least in part by the anchor, wherein the post strand is configured to be pulled to decrease perimeter of the positioning loop to a second size smaller than the first size.

8. The suture construct of claim 1, wherein the suture material passes through the anchor at six locations.

9. A knotless instability suture anchor system, comprising:
   a threader assembly comprising a cover and a back piece with a removably attached threader arm, the cover having at least one movable clip configured to lock into a clip receiving aperture on the back piece;

a channel extending through the threader assembly in both the back piece and the cover;

a hook on the removable threader arm;

a knotless instability suture anchor construct comprising an anchor having a length of suture material passing therethrough, the suture material having a loop strand terminating at a first end and a post strand terminating at a second end, a splice formed through the first end, a sliding construct formed by the first end and the second end, wherein the sliding construct is configured to adjust the relative position of the splice and the anchor;

wherein the knotless instability anchor construct extends along the channel; and a threader loop secured around the hook with ends which extend through the splice and outside the threader assembly.

10. The system of claim 9, further comprising a fixed gap between the splice and the sliding construct.

11. The system of claim 9, wherein the sliding construct is positioned distally to the splice.

12. The system of claim 9, wherein the sliding construct comprises a friction hitch.

13. The system of claim 9, further comprising a driver extending through the channel with the anchor loaded thereon.

14. A method of securing a first body in relative position to a bone hole, the method comprising the steps of:

providing a knotless instability suture anchor construct comprising an anchor having a length of suture material passing therethrough having a loop strand terminating at a first end and a post strand terminating at a second end, a splice formed in the first end, a sliding construct formed by the first end and the second end, wherein the sliding construct creates a positioning loop in the suture material of a first size defined at least in part by I259 and (splice or apperature).clm.the anchor;

passing the first end through the first body and through the splice, creating a locking loop of a first size around the first body;

implanting the anchor into the bone hole;

pulling the post strand to decrease the perimeter of the positioning loop to a second size smaller than the first size;

pulling the loop strand to decrease the perimeter of the locking loop to a second size smaller than the first size; and wherein the step of passing the first end through the first body and through the splice, creating the locking loop of the first size around the first body includes the steps of:

inserting a threader loop through the splice through a first aperture toward the first body;

passing the first end through the threader loop; and pulling the threader loop through the splice and out of a second aperture, wherein the first and second apertures are on the same side of the splice.

15. The method of claim 14, further comprising the step of excising a portion of the first end and the second end.

16. The method of claim 14, wherein the step of pulling the post strand to decrease the perimeter of the positioning loop to the second size smaller than the first size moves the locking loop toward the positioning loop.

17. The method of claim 14, further comprising the step of loading the positioning loop onto a driver.

18. The method of claim 14, wherein the knotless instability suture anchor construct comprises a fixed gap between the splice and the sliding construct.

19. The method of claim 14, wherein the first body is a tissue.

* * * * *